United States Patent
Thomas et al.

(10) Patent No.: US 11,572,575 B2
(45) Date of Patent: Feb. 7, 2023

(54) COMPOSITIONS FOR TRANSFECTING RESISTANT CELL TYPES

(71) Applicant: Precision NanoSystems ULC, Vancouver (CA)

(72) Inventors: Anitha Thomas, New Westminster (CA); Rebecca Anne Grace De Souza, Vancouver (CA); Eric Ouellet, New Westminster (CA); Grace Tharmini Tharmarajah, Toronto (CA); Jagbir Singh, Vancouver (CA); Shyam Madhusudan Garg, Richmond (CA)

(73) Assignee: Precision NanoSystems ULC, Vancouver (CA)

( * ) Notice: Subject to any disclaimer, the term of this patent is extended or adjusted under 35 U.S.C. 154(b) by 316 days.

(21) Appl. No.: 16/349,274

(22) PCT Filed: Dec. 19, 2017

(86) PCT No.: PCT/CA2017/051543
§ 371 (c)(1),
(2) Date: May 12, 2019

(87) PCT Pub. No.: WO2018/119514
PCT Pub. Date: Jul. 5, 2018

(65) Prior Publication Data
US 2019/0292566 A1 Sep. 26, 2019

(51) Int. Cl.
| C12N 15/88 | (2006.01) |
| A61K 9/14 | (2006.01) |
| A61K 9/51 | (2006.01) |
| A61K 47/14 | (2017.01) |
| A61K 47/18 | (2017.01) |
| C12N 5/0793 | (2010.01) |
| C12N 15/11 | (2006.01) |
| C12N 15/113 | (2010.01) |
| C12N 15/85 | (2006.01) |
| C07F 9/10 | (2006.01) |
| C12N 15/87 | (2006.01) |
| C07J 41/00 | (2006.01) |

(52) U.S. Cl.
CPC ........... *C12N 15/88* (2013.01); *A61K 9/14* (2013.01); *A61K 9/5123* (2013.01); *A61K 47/14* (2013.01); *A61K 47/18* (2013.01); *C07F 9/106* (2013.01); *C12N 5/0619* (2013.01); *C12N 15/111* (2013.01); *C12N 15/113* (2013.01); *C12N 15/85* (2013.01); *C12N 15/87* (2013.01); *C07J 41/0055* (2013.01); *C12N 2310/11* (2013.01); *C12N 2310/12* (2013.01); *C12N 2310/14* (2013.01); *C12N 2310/141* (2013.01); *C12N 2310/16* (2013.01); *C12N 2310/531* (2013.01); *C12N 2320/32* (2013.01); *C12N 2500/35* (2013.01); *C12N 2500/36* (2013.01); *C12N 2500/50* (2013.01)

(58) Field of Classification Search
None
See application file for complete search history.

(56) References Cited

U.S. PATENT DOCUMENTS

| 5,527,675 A | 6/1996 | Coull et al. |
| 5,539,082 A | 7/1996 | Nielsen et al. |
| 5,623,049 A | 4/1997 | Löbberding et al. |
| 5,714,331 A | 2/1998 | Buchardt et al. |
| 5,736,336 A | 4/1998 | Buchardt et al. |
| 5,766,855 A | 6/1998 | Buchardt et al. |
| 5,773,571 A | 6/1998 | Nielsen et al. |
| 5,786,461 A | 7/1998 | Buchardt et al. |
| 5,837,459 A | 11/1998 | Berg et al. |
| 5,891,625 A | 4/1999 | Buchardt et al. |
| 5,921,678 A | 7/1999 | Desai et al. |
| 5,972,610 A | 10/1999 | Buchardt et al. |
| 5,981,501 A | 11/1999 | Wheeler et al. |
| 5,986,053 A | 11/1999 | Ecker et al. |
| 6,107,470 A | 8/2000 | Nielsen et al. |
| 6,479,299 B1 | 11/2002 | Parce et al. |
| 6,815,432 B2 | 11/2004 | Wheeler et al. |
| 6,843,942 B2 | 1/2005 | Katinger et al. |
| 8,058,069 B2 | 11/2011 | Yaworski et al. |
| 8,158,601 B2 | 4/2012 | Chen et al. |

(Continued)

FOREIGN PATENT DOCUMENTS

| WO | 9604000 A1 | 2/1996 |
| WO | 03097805 A2 | 11/2003 |

(Continued)

OTHER PUBLICATIONS

Akhtar, S. et al., Interactions of antisense DNA oligonucleotide analogs with phospholipid membranes (liposomes), Nucleic Acids Research, 1991, pp. 5551-5559, vol. 19, No. 20.

(Continued)

*Primary Examiner* — Brian J Davis
(74) *Attorney, Agent, or Firm* — Leydig Voit & Mayer, Ltd.

(57) ABSTRACT

A transfection reagent composition comprising: 30-60 MOL. % of a cationic lipid, or a pharmaceutical acceptable salt thereof; 10-60 MOL % of a structural lipid; 10-20 MOL % of a triglyceride; and 0.1 to about 10 MOL. % of a stabilizing agent, is provided. The transfection agent is effective in transfecting cells, particularly neurons, with siRNA, mRNA and plasmid nucleic acid, Sand maintaining viability of the cells as well as activity of the delivered nucleic acid.

12 Claims, 9 Drawing Sheets

Specification includes a Sequence Listing.

(56) References Cited

U.S. PATENT DOCUMENTS

| | | | |
|---|---|---|---|
| 8,492,359 | B2 | 7/2013 | Yaworski et al. |
| 8,496,961 | B2 | 7/2013 | Hong et al. |
| 8,883,200 | B2 | 11/2014 | Hong et al. |
| D771,833 | S | 11/2016 | Leaver et al. |
| D771,834 | S | 11/2016 | Leaver et al. |
| D772,427 | S | 11/2016 | Leaver et al. |
| 9,758,795 | B2 | 9/2017 | Cullis et al. |
| 2003/0077829 | A1 | 4/2003 | MacLachlan |
| 2004/0262223 | A1 | 12/2004 | Strook et al. |
| 2005/0175683 | A1 | 8/2005 | Zhang |
| 2007/0087045 | A1 | 4/2007 | Li et al. |
| 2008/0241917 | A1* | 10/2008 | Akita ............... A61K 9/1272 435/320.1 |
| 2010/0022680 | A1 | 1/2010 | Karnik et al. |
| 2011/0182994 | A1 | 7/2011 | Kornfield et al. |
| 2012/0270921 | A1 | 10/2012 | de Fougerolles et al. |
| 2012/0276209 | A1 | 11/2012 | Cullis et al. |
| 2013/0303587 | A1 | 11/2013 | Yaworski et al. |
| 2013/0323269 | A1 | 12/2013 | Manoharan et al. |
| 2014/0328759 | A1 | 11/2014 | Cullis et al. |
| 2016/0022580 | A1 | 1/2016 | Ramsay et al. |
| 2016/0235688 | A1 | 8/2016 | Walsh et al. |
| 2016/0250354 | A1 | 9/2016 | Manoharan et al. |

FOREIGN PATENT DOCUMENTS

| | | |
|---|---|---|
| WO | 2009086558 A1 | 7/2009 |
| WO | 2009127060 A1 | 10/2009 |
| WO | 2011000106 A1 | 1/2011 |
| WO | 2012000104 A1 | 1/2012 |
| WO | 2012016184 A2 | 2/2012 |
| WO | WO 2014/172045 A1 | 10/2014 |
| WO | 2017117647 A1 | 7/2017 |
| WO | WO 2017/218704 A1 | 12/2017 |
| WO | WO 2018/064755 A1 | 4/2018 |

OTHER PUBLICATIONS

Bassit, A. C. Ferreira et al., The Potential Use of Nanoparticles for Noggin SiRNA Delivery to Accelerate Bone Formation in Distraction Osteogenesis, J Nanomed Nanotechnol, 2015, pp. 1-8, 6:1, http://dx.doi.org/10.4172/2157-7439.1000257.

Belliveau, N. M. et al., Microfluidic Synthesis of Highly Potent Limit-Size Lipid Nanoparticles for In Vivo Delivery of siRNA,. Molecular Therapy—Nucleic Acids, 2012, pp. 1-9, vol. 1, No. 8.

Bunjes H. et al., Effects of surfactants on the crystallization and polymorphism of lipid nanoparticles, Progr Colloid Polym Sci, 2002, pp. 7-10, vol. 121.

Heyes, J., et al., Lipid Encapsulation Enables the Effective Systemic Delivery of Polyplex Plasmid DNA, Molecular Therapy, 2007, pp. 713-720, vol. 15(4).

Jahn A., et al., Preparation of Nanoparticles by Continuous-Flow Microfluidics. Journal of Nanoparticle Research, 2008, pp. 925-934. vol. 10, No. 6.

Jeffs, L. B., et al., A Scalable, Extrusion-Free Method for Efficient Liposomal Encapsulation of Plasmid DNA, Pharmaceutical Research, 2005, pp. 362-372, vol. 22(3).

Kaufman, K. J. et al., Materials for non-viral intracellular delivery of messenger RNa therapeutics, J Controlled Release, 2016, pp. 227-234, vol. 240.

Kauffman, K. J. et al., Optimization of Lipid Nanoparticle Formulations for mRNA Delivery in Vivo with Fractional Factorial and Definitive Screening Designs, NANO letters, 2015, pp. 7300-7306, vol. 15.

Leung, A. K. K. et al., Microfluidic Mixing: A General Method for Encapsulating Macromolecules in Lipid Nanoparticle Systems., J. Phys. Chem. B, 2015, pp. 8698-8706, vol. 119.

Lv, H. et al., Toxicity of cationic lipids and cationic polymers in gene delivery, Journal of Controlled Release, 2006, pp. 100-109, vol. 114(1).

Mingozzi, F. et al., Immune responses to AAV vectors: overcoming barriers to successful gene therapy, Blood, 2013, pp. 23-36, vol. 122, No. 1.

Montana, G. et al. Employment of cationic solid-lipid nanoparticles as RNA carriers. Bioconjugate Chem, 2007, pp. 302-308, vol. 18, No. 2.

O'Mahony, A. M. et al., Non-viral nanosystems for gene and small interfering RNA delivery to the central nervous system: formulating the solution, J Pharm Sci, 2013, pp. 3469-3484, vol. 102, No. 10.

Stroock, A. D. et al. Chaotic mixer for microchannels, Science, 2002, pp. 647-651, vol. 295.

Szoka, F. Jr, and Papahadjopoulos, D, Comparative properties and methods of preparation of lipid vesicles (liposomes), Annu Rev Biophys Bioeng, 1980, pp. 467-508, vol. 9.

Tam, Y. Y. C. et al., Advances in Lipid nanoparticles for siRNA Delivery, Pharmaceutics, 2013, pp. 498-507, vol. 5, doi:10.3390/pharmaceutics5030498.

Xu, Y. et al., Physicochemical characterization and purification of cationic lipoplexes, Biophysical Journal, 1999, pp. 341-353, vol. 77, No. 1.

European Patent Office, Extended European Search Report in counterpart European Patent Application No. 19796018.0, dated Oct. 15, 2021.

* cited by examiner

SEQUENCE LISTING

<160> NUMBER OF SEQ ID NOS: 6

<210> SEQ ID NO 1
<211> LENGTH: 966
<212> TYPE: DNA
<213> ORGANISM: Artificial
<220> FEATURE:
<223> OTHER INFORMATION: mRNA eGFP ORF
<220> FEATURE:
<221> NAME/KEY: misc_feature
<222> LOCATION: (721)..(846)
<223> OTHER INFORMATION: n is a, c, g, t or u

<400> SEQUENCE: 1

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
```

```
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaa                                                               966

<210> SEQ ID NO 2
<211> LENGTH: 25
<212> TYPE: DNA
<213> ORGANISM: Artificial
<220> FEATURE:
<223> OTHER INFORMATION: HPRT siRNA first strand

<400> SEQUENCE: 2
gccagacuuu guuggauuug aaatt                                           25

<210> SEQ ID NO 3
<211> LENGTH: 26
<212> TYPE: DNA
<213> ORGANISM: Artificial
<220> FEATURE:
<223> OTHER INFORMATION: HPRT siRNA second strand

<400> SEQUENCE: 3
aauuucaauc caacaaaguc uggcuu                                          26

<210> SEQ ID NO 4
<211> LENGTH: 23
<212> TYPE: DNA
<213> ORGANISM: Artificial
<220> FEATURE:
<223> OTHER INFORMATION: Sense strand for DsiNC-1 control

<400> SEQUENCE: 4
cguuaaucgc guauaauacg cgu                                             23

<210> SEQ ID NO 5
<211> LENGTH: 27
<212> TYPE: DNA
<213> ORGANISM: Artificial
<220> FEATURE:
<223> OTHER INFORMATION: Antisense strand for DsiNC

<400> SEQUENCE: 5
auacgcguau uauacgcgau uaacgac                                         27

<210> SEQ ID NO 6
<211> LENGTH: 3487
```

```
<212> TYPE: DNA
<213> ORGANISM: Artificial
<220> FEATURE:
<223> OTHER INFORMATION: Circular dsDNA pCMV-GFP

<400> SEQUENCE: 6
tagttattaa tagtaatcaa ttacggggtc attagttcat agcccatata tggagttccg    60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggag tatttacggt aaactgccca cttggcagta catcaagtgt atcatatgcc   240
aagtccgccc cctattgacg tcaatgacgg taaatggccc gcctggcatt atgcccagta   300
catgacctta cggactttcc tacttggcag tacatctacg tattagtca tcgctattac   360 catggtgatg cggttttggc agtacaccaa tgggcgtgga tagcggtttg actcacgggg   420
atttccaagt ctccacccca ttgacgtcaa tgggagtttg ttttggcacc aaaatcaacg   480
ggactttcca aaatgtcgta ataaccccgc cccgttgacg caaatgggcg taggcgtgt    540 acggtgggag gtctatataa gcagaggtcg tttagtgaac cgtcagatca ctagtagctt   600
tattgcggta gtttatcaca gttaaattgc taacgcagtc agtgctcgac tgatcacagg   660
taagtatcaa ggttacaaga caggtttaag gaggccaata gaaactgggc ttgtcgagac   720
agagaagatt cttgcgtttc tgataggcac ctattggtct tactgacatc cactttgcct   780
ttctctccac aggggtaccg aagccgctag cgctaccggt cgccaccatg cccgccatga   840
agatcgagtg ccgcatcacc ggcaccctga acggcgtgga gttcgagctg gtgggcggcg   900 agagggcac ccccgagcag ggccgcatga ccaacaagat gaagagcacc aaaggcgccc   960
tgaccttcag cccctacctg ctgagccacg tgatgggcta cggcttctac cacttcggca  1020 cctacccag cggctacgag aaccccttcc tgcacgccat caacaacggc ggctacacca  1080
acacccgcat cgagaagtac gaggacggcg gcgtgctgca cgtgagcttc agctaccgct  1140
acgaggccgg ccgcgtgatc ggcgacttca aggtggtggg caccggcttc cccgaggaca  1200
gcgtgatctt caccgacaag atcatccgca gcaacgccac cgtggagcac ctgcacccca  1260
tgggcgataa cgtgctggtg gcagcttcg cccgcacctt cagcctgcgc gacggcggct  1320
actacagctt cgtggtggac agccacatgc acttcaagag cgccatccac cccagcatcc  1380
tgcagaacgg ggccccatg ttcgccttcc gccgcgtgga ggagctgcac agcaacaccg  1440
agctgggcat cgtggagtac cagcacgcct tcaagacccc catcgccttc gccagatctc  1500
gagctcgatg agtttggaca aaccacaact agaatgcagt gaaaaaaatg ctttatttgt  1560
gaaatttgtg atgctattgc tttatttgta accattataa gctgcaataa acaagttaac  1620
aacaacaatt gcattcattt tatgtttcag gttcagggg aggtgtggga ggttttttaa  1680
agcaagtaaa acctctacaa atgtggtact taagaggggg agaccaaagg gcgagacgtt  1740
aaggcctcac gtgacatgtg agcaaaaggc cagcaaaagg ccaggaaccg taaaaaggcc  1800
gcgttgctgg cgttttccca taggctccgc cccctgacg agcatcacaa aaatcgacgc  1860
tcaagtcaga ggtggcgaaa cccgacagga ctataaagat accaggcgtt ccccctgga  1920 agctccctcg tgcgctctcc tgttccgacc ctgccgctta cgggatacct gtccgccttt  1980
ctcccttcgg gaagcgtggc gctttctcat agctcacgct gtaggtatct cagttcggtg  2040
taggtcgttc gctccaagct gggctgtgtg cacgaacccc ccgttcagcc cgaccgctgc  2100
gccttatccg gtaactatcg tcttgagtcc aacccggtaa gacacgactt atcgccactg  2160
```

```
gcagcagcca ctggtaacag gattagcaga gcgaggtatg taggcggtgc tacagagttc  2220
ttgaagtggt ggcctaacta cggctacact agaagaacag tatttggtat ctgcgctctg  2280
ctgaagccag ttaccttcgg aaaaagagtt ggtagctctt gatccggcaa acaaaccacc  2340
gctggtagcg gtggtttttt tgtttgcaag cagcagatta cgcgcagaaa aaaaggatct  2400
caagaagatc ctttgatctt ttctacgggg tctgacgctc agtggaacga aaactcacgt  2460
taagggattt tggtcatgcc gtctcagaag aactcgtcaa gaaggcgata gaaggcgatg  2520
cgctgcgaat cgggagcggc gataccgtaa agcacgagga gcggtcagc ccattcgccg  2580 ccaagctctt cagcaatatc acgggtagcc aacgctatgt cctgatagcg gtccgccaca  2640
cccagccggc cacagtcgat gaatccagaa aagcggccat tttccaccat gatattcggc  2700
aagcaggcat cgccatgggt cacgacgaga tcctcgccgt cgggcatgct cgccttgagc  2760
ctggcgaaca gttcggctgg cgcgagcccc tgatgctctt cgtccagatc atcctgatcg  2820
acaagaccgg cttccatccg agtacgtgct ctctcgatgc gatgtttcgc ttggtggtcg  2880
aatgggcagg tagccggatc aagcgtatgc agccgccgca ttgcatcagc catgatggat  2940
actttctcgg caggagcaag gtgagatgac aggagatcct gccccggcac ttcgcccaat  3000
agcagccagt cccttcccgc ttcagtgaca acgtcgagta cagctgcgca aggaacgccc  3060
gtcgtggcca gccacgatag ccgcgctgcc tcgtcttgca gttcattcag ggcaccggac  3120
aggtcggtct tgacaaaaag aaccgggcgc ccctgcgctg acagccggaa cacggcggca  3180
tcagagcagc cgattgtctg ttgtgcccag tcatagccga atagcctctc cacccaagcg  3240
gccggagaac ctgcgtgcaa tccatcttgt tcaatcataa tattattgaa gcatttatca  3300
gggttcgtct cgtcccggtc tcctcccatg catgtcaata ttggccatta gccatattat  3360
tcattggtta tatagcataa atcaatattg gctattggcc attgcatacg ttgtatctat  3420
atcataatat gtacatttat attggctcat gtccaatatg accgccatgt tggcattgat  3480
tattgac                                                            3487
```

COMPOSITIONS FOR TRANSFECTING RESISTANT CELL TYPES

CROSS-REFERENCE TO RELATED APPLICATIONS

The present application is a U.S. national phase application under 35 U.S.C. 371 of international PCT application number PCT/US2017/051543, filed Dec. 19, 2017, which claims priority under 35 U.S.C. § 119(e) of U.S. provisional patent application 62/439,847, filed on Dec. 28, 2016, the specification of which is hereby incorporated by reference.

This application claims the benefit of U.S. application No. 62/439,847 filed on Dec. 28, 2016.

BACKGROUND OF THE INVENTION

Field of Invention

The field of the invention is the transfer of active nucleic acids into cells.

Related Art

Nucleic acids in the form of polynucleotides or oligonucleotides can be used to focus treatment on a particular genetic target, either by interfering with its expression, or by restoring or augmenting its expression, or by editing the gene.

Delivering nucleic acids into cells or tissues presents challenges because nucleic acids are relatively large, negatively charged, hydrophilic compounds which are not capable of passively diffusing across the cell membrane and are also vulnerable to nucleases. (Akhtar, Basu S Fau—Wickstrom et al. 1991)

Existing approaches for delivering these nucleic acids across the cell membrane include viruses such as adeno-associated viruses as vectors for gene restoration, but these can cause immune responses in treated individuals (Mingozzi and High 2013). Cationic lipids and polymers have also been used in experiments, but each has issues of transfection efficiency, stability and toxicity (Lv, Zhang et al. 2006). To increase the therapeutic activity of the nucleic acids, significant efforts in the field have focused on lipid nanoparticles (LNP) that comprise cationic lipids, including ionisable cationic lipids (also known as "cationic lipids") and PEGylated lipids, for the efficient encapsulation and delivery of nucleic acids to cells (Tam, Chen et al. 2013, Kauffman, Webber et al. 2015).

LNPs have been engineered to obtain different pharmacokinetics, different biodistribution in tissues, biodegradability, or altered toxicity, to favor the therapeutic activity of the nucleic acid. Triolein has been tested in 1-palmitoyl-2-oleoyl-sn-glycero-3-phosphocholine micelle size-ranging experiments.

CNS tissue is notoriously difficult to transfect (O'Mahony, Godinho et al. 2013). The cells are sensitive to their conditions and are hard to maintain in vitro. A more effective method for effectively delivering nucleic acids into neurons is still required.

SUMMARY OF THE INVENTION

According to embodiments of the invention, there is provided a composition for transfecting nucleic acid into live cells including: 30-50 mol % of a cationic lipid or pharmaceutically acceptable salt thereof; 10-50 mol % of a structural lipid; 5 to 40% mol % of a triglyceride; and 0.1 to about 10 mol % of a stabilizing agent. In embodiments, the cationic lipid is an amino lipid or a pharmaceutically acceptable salt thereof. In embodiments, the cationic lipid is 1,17-bis(2-octylcyclopropyl)heptadecan-9-yl-4-(dimethylamino). In embodiments, the structural lipid is selected from diacylphosphatidylcholines, diacylphosphatidylethanolamines, ceramides, sphingomyelins, dihydrosphingomyelins, cephalins, and cerebrosides. In embodiments, the triglyceride is selected from the group consisting of triolein, tristearin, trilaurin, trilinoein, trilinolenin, trimyristin, tripalmitin, tricaprylin, and oleoyldipalmitin. In embodiments, the stabilizing agent is selected from PEG-lipid conjugates, polyoxyethylene alkyl ethers, diblock polyoxyethylene ether co-polymers, triblock polyoxyethylene alkyl ethers co-polymers, and amphiphilic branched polymers. In embodiments, the PEG-lipid is selected from the group consisting of PEG-ceramide, PEG-DMG, PEG-PC, PEG-PE, and PEG-DMA. In embodiments, the stabilizing agent is selected from polyoxyethylene (20) oleyl ether, polyoxyethylene (23) lauryl ether, polyoxyethylene (40) stearate ("Myrj52"), poly(propylene glycol)11-block-poly(ethylene glycol)16-block-poly(propylene glycol)11, poly(propylene glycol)12-block-poly(ethylene glycol)28-block-poly(propylene glycol)12.

In embodiments, the composition further including a sterol, for example, cholesterol.

In embodiments of the invention, the cationic lipid is about 40 mol % of the composition. In embodiments of the invention, the triglyceride is from about 1 to about 50 mol % of the composition.

In embodiments of the invention, the cationic lipid is 1,17-bis(2-octylcyclopropyl)heptadecan-9-yl-4-(dimethylamino) butanoate or a pharmaceutically acceptable salt thereof. In embodiments of the invention, the structural lipid makes up 20 to 40 mol % of the composition. In embodiments of the invention, the triglyceride is triolein. In embodiments of the invention, the stabilizing agent is 1 to 5 mol % polyoxyethylene (40) stearate (a.k.a. "Myrj52"). In embodiments of the invention, the stabilizing lipid includes about 2.5 mole percent of polyoxyethylene (40) stearate.

In embodiments of the invention, the structural lipid is DOPE. In embodiments of the invention, the structural lipid is DSPE.

In embodiments of the invention, the composition further includes a nucleic acid. In embodiments, the nucleic acid is DNA. In other embodiments, the nucleic acid is an RNA. In other embodiments, the nucleic acid is a locked nucleic acid. In yet other embodiments, the nucleic acid is a nucleic acid analog. In other embodiments, the nucleic acid is a plasmid. In embodiments of the invention, the nucleic acid is circular. In other embodiments of the invention, the nucleic acid is linear.

In embodiments of the invention, the composition exists in the form of nanoparticles having a diameter of from about 15 nm to about 300 nm.

In embodiments of the invention, a method for introducing a nucleic acid into a cell is provided, which method maintains activity of the nucleic acid and viability of the cell. In embodiments, the method include contacting the cell with the embodiment compositions.

In still other embodiments, a method is provided for modulating the expression of a target polynucleotide or polypeptide in a cell while maintaining cell viability, which method includes contacting the cell with the composition embodiments of the invention. In embodiments, the cell is a neuron. In embodiments, the cell is a mammalian cell. In embodiments, the transfecting occurs in vitro. In embodiments, the transfecting occurs in vivo.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Figure 1:
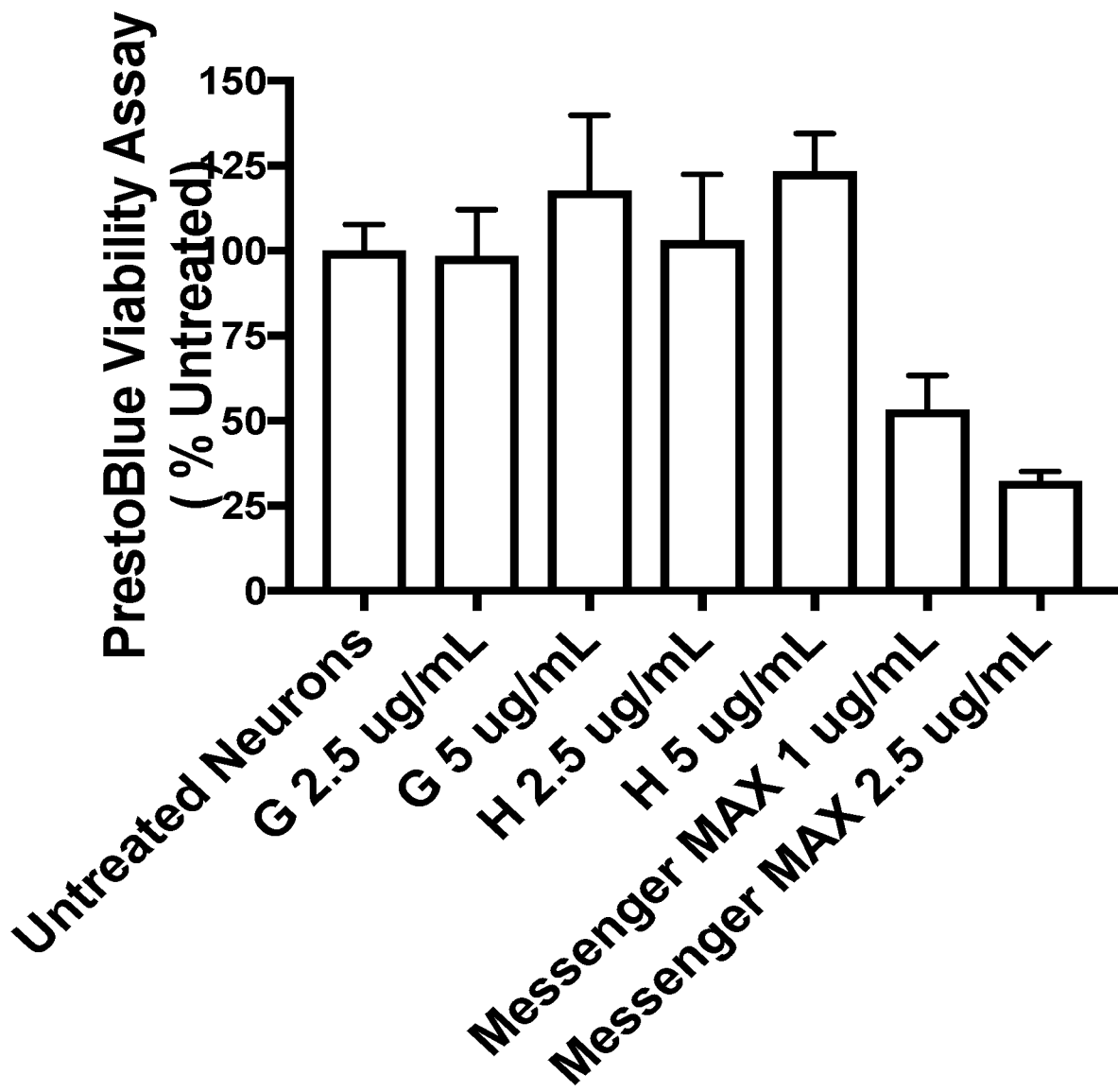
FIG. 1 is a bar graph of in vitro neuron viability demonstrated by PrestoBlue assay under seven conditions at 48 h: no treatment, treatment with Lipid Mix G GFP mRNA LNP, treatment with Lipid Mix H GFP mRNA LNP and treatment with commercial reagent MessengerMax™ Lipofectamine™ (2.5 ug/mL or 5 ug/mL of LNP, 1 ug/mL or 2.5 ug/mL of Messenger Max)+5 ug/mL ApoE.

The present invention provides compositions, lipid nanoparticles containing a therapeutic agent, methods for making the lipid nanoparticles containing a therapeutic agent, methods for targeting specific cell types, and methods for delivering a therapeutic agent using the lipid nanoparticles.

In one aspect, there is provided a lipid mix composition that includes one or more cationic lipid(s), one or more structural lipid(s), and one or more stabilizing agent(s).

In another aspect, the lipid mix compositions of the invention are provided for mixing with nucleic acid therapeutics for delivery to target cells or tissues, or for treatment of mammals in need of such delivery for treatment of insufficiency or disease.

In another aspect, the lipid mix further includes one or more triglyceride(s).

In another aspect, the lipid mix compositions according the invention are provided for formulating nucleic acid therapeutics for the treatment of diseases of the CNS.

"Neurons" in this application mean mature neurons, neural progenitor cells, and are characterized by electrical excitability and the presence of membrane junctions that transmit signals to other cells (synapses).

"Lipid" refers to a group of organic compounds that are based on fatty acids, and are characterized by being insoluble in water but soluble in many organic solvents.

Lipid Particles. The invention provides lipid nanoparticles manufactured from the compositions described above. The lipid nanoparticles contain a therapeutic agent in some embodiments. The lipid nanoparticles include one or more cationic lipids, one or more structural lipid(s), one or more stabilizing agent(s), and one or more nucleic acids.

Cationic lipid. The lipid nanoparticles include a cationic lipid. As used herein, the term "cationic lipid" refers to a lipid that is cationic or becomes ionizable (protonated) as the pH is lowered below the pK of the cationic group of the lipid, but is progressively more neutral at higher pH values. At pH values below the pK, the lipid is then able to associate with negatively charged nucleic acids (e.g., oligonucleotides). As used herein, the term "cationic lipid" includes zwitterionic lipids that assume a positive charge on pH decrease, and any of a number of lipid species which carry a net positive charge at a selective pH, such as physiological pH. Such lipids include, but are not limited to N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB); N-(2,3-dioleoyloxy)propyl)-N,N,N-trimethylammonium chloride (DOTAP); 3-(N—(N',N'-dimethylaminoethane)-carbamoyl)cholesterol (DC-Chol), C12-200 and N-(1,2-dimyristyloxyprop-3-yl)-N,N-dimethyl-N-hydroxyethyl ammonium bromide (DMRIE).

In one embodiment, the cationic lipid is an amino lipid. Suitable amino lipids useful in the invention include those described in WO 2009/096558, incorporated herein by reference in its entirety. Representative amino lipids include 1,17-bis(2-octylcyclopropyl)heptadecan-9-yl 4-(dimethylamino)butanoate hydrochloride, 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), and 2,2-dilinoleyl-4-dimethylaminomethyl-[1,3]-dioxolane (DLin-K-DMA).

Suitable amino lipids include those having the general formula:

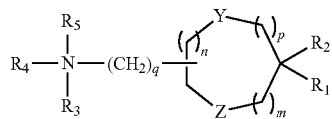

wherein $R_1$ and $R_2$ are either the same or different and independently optionally substituted $C_{10}$-$C_{24}$ alkyl, optionally substituted $C_{10}$-$C_{24}$ alkenyl, optionally substituted $C_{10}$-$C_{24}$ alkynyl, or optionally substituted $C_{10}$-$C_{24}$ acyl;
$R_3$ and $R_4$ are either the same or different and independently optionally substituted $C_1$-$C_6$ alkyl, optionally substituted $C_2$-$C_6$ alkenyl, or optionally substituted $C_2$-$C_6$ alkynyl or $R_3$ and $R_4$ may join to form an optionally substituted heterocyclic ring of 4 to 6 carbon atoms and 1 or 2 heteroatoms chosen from nitrogen and oxygen;
$R_5$ is either absent or present and when present is hydrogen or $C_1$-$C_6$ alkyl;
m, n, and p are either the same or different and independently either 0 or 1 with the proviso that m, n, and p are not simultaneously 0;
q is 0, 1, 2, 3, or 4; and Y and Z are either the same or different and independently O, S, or NH.

In one embodiment, $R_1$ and $R_2$ are each linoleyl, and the amino lipid is a dilinoleyl amino lipid. In one embodiment, the amino lipid is a dilinoleyl amino lipid.

In embodiments of the invention, the cationic lipid is 1,17-bis(2-octylcyclopropyl)heptadecan-9-yl 4-(dimethylamino)butanoate hydrochloride. This compound is disclosed in United States Published Application 2013323269.

In other embodiments, the cationic lipid-like material is C12-200 as described by Kaufmann and his colleagues (Kaufmann k 2015)

The cationic lipid is present in embodiments of the composition and lipid particle of the invention comprise an amount from about 30 to about 60 mole percent ("MOL %", or the percentage of the total moles that is of a particular component), preferably from 30 to 50 MOL %. In preferred embodiments, the cationic lipid is present in 40 MOL %.

Structural lipids. The composition and lipid nanoparticles of the invention include one or more structural lipids. Suitable structural lipids support the formation of particles during manufacture. Structural lipids refer to any one of a number of lipid species that exist in either in an anionic, uncharged or neutral zwitterionic form at physiological pH. Representative structural lipids include diacylphosphatidylcholines, diacylphosphatidylethanolamines, diacylphosphatidylglycerols, ceramides, sphingomyelins, dihydrosphingomyelins, cephalins, and cerebrosides.

Exemplary structural lipids include zwitterionic lipids, for example, distearoylphosphatidylcholine (DSPC), dioleoylphosphatidylcholine (DOPC), dipalmitoylphosphatidylcholine (DPPC), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoyl-phosphatidyethanol amine (SOPE), and 1,2-dielaidoyl-sn-glycero-3-phophoethanolamine (transDOPE).

In one embodiment, the structural lipid is 1,2-dioleoyl-sn-glycero-3-phosphoethanolamine (DOPE).

In one embodiment the structural lipid may be any lipid that is negatively charged at physiological pH. These lipids include phosphatidylglycerol such as dioleoylphosphatidylglycerol (DOPG), dipalmitoylphosphatidylglycerol (DPPG), palmitoyloleyolphosphatidylglycerol (POPG), cardiolipin, phosphatidylinositol, diacylphosphatidylserine, diacylphosphatidic acid, other anionic modifying groups joined to neutral lipids.

Stabilizing Agents are included in compositions and lipid nucleic acid embodiments to ensure integrity of the mixture. Stabilizing agents, in some embodiments of the invention, are polyethylene glycol-lipids. Suitable polyethylene glycol-lipids include PEG-modified phosphatidylethanolamine, PEG-modified phosphatidic acid, PEG-modified ceramides (e.g., PEG-CerC$_{14}$ or PEG-CerC$_{20}$), PEG-modified dialkylamines, PEG-modified diacylglycerols, PEG-modified dialkylglycerols. Representative polyethylene glycol-lipids include PEG-c-DOMG, PEG-c-DMA, and PEG-s-DMG. In one embodiment, the polyethylene glycol-lipid is

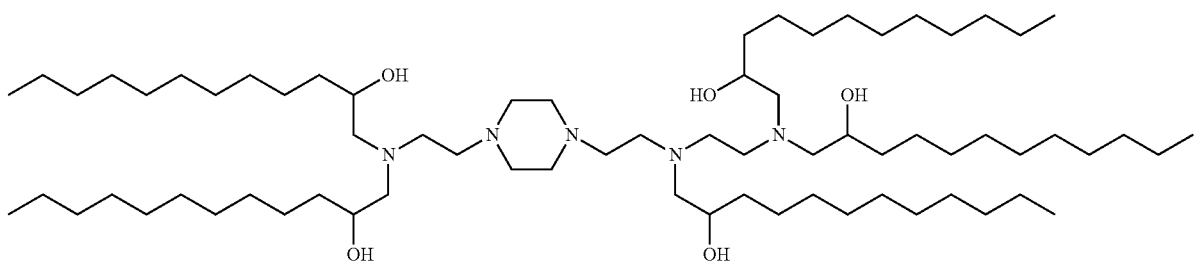 [SMILES: CCCCCCCCCCC(O)CN(CCN1CCN(CCN(CC(O)CCCCCCCCCC)CC(O)CCCCCCCCCC)CC1)CCN(CC(O)CCCCCCCCCC)CC(O)CCCCCCCCCC]

N-[(methoxy poly(ethylene glycol)$_{2000}$)carbamyl]-1,2-dimyristyloxlpropyl-3-amine (PEG-c-DMA).

In one embodiment, the polyethylene glycol-lipid is PEG-c-DOMG. In another embodiment, the polyethylene glycol-lipid is PEG-DMG (1,2-Dimyristoyl-sn-glycerol, methoxy-polyethylene glycol). In some embodiments, the polyethylene glycol lipid content is from 0 to 10% of the Lipid Mix.

In embodiments, the stabilizing agent is polyoxyethylene alkyl ether, diblock polyoxyethylene ether co-polymer, tri-block polyoxyethylene alkyl ethers co-polymer, or amphiphilic branched polymers. In particular embodiments, the stabilizing agent is polyoxyethylene (20) oleyl ether, polyoxyethylene (23) lauryl ether, polyoxyethylene (40) stearate, poly(propyleneglycol) 11-block-poly (ethyleneglycol) 16-block-poly(propylene glycol)11, poly(propylene glycol) 12-block-poly(ethylene glycol)28-block-poly(propylene glycol)12.

Sterols are included in some embodiments of the compositions, and lipid nanoparticles made therefrom include sterols, such as cholesterol.

Other suitable structural lipids include glycolipids (e.g., monosialoganglioside GM$_1$).

In certain embodiments, the structural lipid is present in the lipid particle in an amount from about 20 to about 40 MOL %. In one embodiment, the structural lipid is present in the lipid particle in an amount from about 20 to about 30 MOL %. In one embodiment, the structural lipid is present in the lipid particle in about 20 MOL %, or in about 30 MOL %, or in about 40 MOL %. In embodiments of the invention, the cationic lipid was 1,17-bis(2-octylcyclopropyl)heptadecan-9-yl 4-(dimethylamino)butanoate hydrochloride and the structural lipid (DOPE, for example) was 20, 30 or 40 MOL %.

Surprisingly, the addition of 10 to 20 mole percent of triolein to the lipid mix resulted in increased target cell viability when added to compositions and lipid nucleic acid particles of the invention. The addition of this triglyceride also surprisingly enhanced mRNA expression in target cells.

Triglycerides are esters of fatty acids with glycerol. Tristearin, trilaurin, trilinoein, trilinolenin, trimyristin, tripalmitin, tricaprylin, oleoyldipalmitin are examples. All three fatty acids can be the same or different. Triglyceride can be symmetric or asymmetric. SSS, SUS, and USU-triglycerides are considered symmetric triglycerides, where S represents a saturated fatty acid and U represents an unsaturated fatty acid. If the sn-1 and sn-3 position contain different fatty acids, then the central carbon atom is a chiral carbon, and is asymmetric. A fatty acid is a carboxylic acid with a long aliphatic chain consisting of 4-28 even number of carbons, comprising short, medium or long chain saturated or unsaturated triglyceride, given embodiment may contain more importantly 12-22 carbon atoms. Examples of common fatty acids include, but are not limited to, linoleic acid, linolenic acid, oleic acid, palmitic acid, lauric acid, stearic acid, behenic acid, arachidonic acid, etc. The fatty acid can be unsaturated or saturated. Triglycerides can be naturally derived or synthesized. Example of natural origin fatty acids include omega 3 fatty acid, omega 6 fatty acid, etc. Examples of an omega3 fatty acids are alpha-linolenic acid, docasahexaenoic acid. Examples of omega6 fatty acids are linoleic acid, and gamma linolenic acid. Triglycerides can also be part of compounds classified under the following trade names: Captex®, Sterotex®, and others.

In embodiments of the invention, the triglyceride is triolein (TO), a symmetrical triglyceride derived from glycerol and three units of the unsaturated fatty acid oleic acid. The IUPAc name for triolein is 2,3-bis[[(Z)-octadec-9-enoyl]oxy]propyl (Z)-octadec-9-enoate, and synonyms include glycerol trioleate, glycerol, trioleyl, trielaidin, trioleoylglycerol, and trioleyl glycerol. In other embodiments of the invention, triolien is replaced by another symmetrical triglyceride such as one or a mixture of tristearin, trilaurin, trilinoein, trilinolenin, trimyristin, tripalmitin, tricaprylin, or oleoyldipalmitin.

In one embodiment of the invention, a mix of triglycerides are included in the lipid mix composition.

Nucleic Acids. The lipid mix compositions and lipid nanoparticles of the present invention are useful for the systemic or local delivery of nucleic acid therapeutics. As described herein, the nucleic acid therapeutic (NAT) is incorporated into the lipid particle during its formation.

As used herein, the term "nucleic acid therapeutic" (NAT) is meant to include any oligonucleotide or polynucleotide whose delivery into a cell causes a desirable effect. Fragments containing up to 50 nucleotides are generally termed oligonucleotides, and longer fragments are called polynucleotides. In particular embodiments, oligonucleotides of the present invention are 20-50 nucleotides in length. In other embodiments of the invention, oligonucleotides are 996 to 4500 nucleotides in length, as in the case of messenger RNA or plasmids. In the context of this invention, the terms "polynucleotide" and "oligonucleotide" refer to a polymer or oligomer of nucleotide or nucleoside monomers consisting of naturally occurring bases, sugars and intersugar (backbone) linkages. The terms "polynucleotide" and "oligonucleotide" also include polymers or oligomers comprising non-naturally occurring monomers, or portions thereof, which function similarly. Such modified or substituted oligonucleotides are often preferred over native forms because of properties such as enhanced cellular uptake and increased stability in the presence of nucleases. Oligonucleotides are classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose. The nucleic acid that is present in a lipid particle according to this invention includes single-stranded DNA or RNA, or double-stranded DNA or RNA, or DNA-RNA hybrids. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include antisense oligonucleotides, ribozymes, microRNA, mRNA, and triplex-forming oligonucleotides.

In one embodiment, the polynucleic acid is an antisense oligonucleotide. In certain embodiments, the nucleic acid is a ribozyme, a non-coding nuclear or nucleolar RNA as explained in HUGO http://www.genenames.org/cgi-bin/genefamilies, miRNA, rRNA, tRNA, siRNA, saRNA, snRNA, snoRNA, lncRNA, piRNA, tsRNA, srRNA, crRNA, tracrRNA, sgRNA, shRNA, ncRNA, miRNA, mRNA, pre-condensed DNA, pDNA, an aptamer, or a combination thereof. In one embodiment, the nucleic acid therapeutic (NAT) is a plasmid or circular nucleic acid construct. In one embodiment, the NAT is a mRNA. In one embodiment, the NAT is a siRNA. In one embodiment, the NAT is a miRNA. In one embodiment, the NAT is a tracrRNA. In one embodiment, the NAT is a sgRNA.

The term "nucleic acids" also refers to ribonucleotides, deoxynucleotides, modified ribonucleotides, modified deoxyribonucleotides, modified phosphate-sugar-backbone oligonucleotides, other nucleotides, nucleotide analogs, and combinations thereof, and can be single stranded, double stranded, or contain portions of both double stranded and single stranded sequence, as appropriate. In one embodiment, the nucleic acid exists in a circular plasmid structure.

As used herein, the terms "polynucleotide" and "oligonucleotide" are used interchangeably and mean single-stranded and double-stranded polymers of nucleotide monomers, including 2'-deoxyribonucleotides (DNA) and ribonucleotides (RNA) linked by internucleotide phosphodiester bond linkages, e.g., 3'-5' and 2'-5', inverted linkages, e.g., 3'-3' and 5'-5', branched structures, or internucleotide analogs. Polynucleotides have associated counter ions, such as $H+$, $NH4+$, trialkylammonium, $Mg2+$, $Na+$, and the like. A polynucleotide may be composed entirely of deoxyribonucleotides, entirely of ribonucleotides, or chimeric mixtures thereof.

Preferred nucleic acids are DNA and RNA.

As used herein, nucleic acids may also refer to "peptide nucleic acid" or "PNA" means any oligomer or polymer segment (e.g., block oligomer) comprising two or more PNA subunits (residues), but not nucleic acid subunits (or analogs thereof), including, but not limited to, any of the oligomer or polymer segments referred to or claimed as peptide nucleic acids in U.S. Pat. Nos. 5,539,082; 5,527,675; 5,623,049; 5,714,331; 5,718,262; 5,736,336; 5,773,571; 5,766,855; 5,786,461; 5,837,459; 5,891,625; 5,972,610; 5,986,053; and 6,107,470; all of which are herein incorporated by reference. The term "peptide nucleic acid" or "PNA" also applies to any oligomer or polymer segment comprising two or more subunits of those nucleic acid mimics such as those described in Peptide-Based Nucleic Acid Mimics (PENAMS) of Shah et al. as disclosed in WO96/04000.

The lipid nanoparticles (LNP) according to some embodiments of the invention can also be characterized by electron microscopy. The LNP of the invention have a substantially solid core with an electron dense core when viewed by electron microscopy. One such structure is disclosed in U.S. Pat. No. 9,758,795 by Cullis et al. Electron dense is defined such that area-averaged electron density of the interior 50% of the projected area of a solid core particle (as seen in a 2-D cryo EM image) is not less than x % (x=20%, 40%, 60%) of the maximum electron density at the periphery of the particle. Electron density is calculated as the absolute value of the difference in image intensity of the region of interest from the background intensity in a region containing no nanoparticle.

The lipid nanoparticles of the invention have a diameter (mean particle diameter) from about 15 to about 300 nm. In some embodiments, the mean particle diameter is greater than 300 nm. In some Embodiments, the lipid particle has a diameter of about 300 nm or less, 250 nm or less, 200 nm or less, 150 nm or less, 100 nm or less, or 50 nm or less. In one embodiment, the lipid particle has a diameter from about 50 to about 150 nm. These smaller particles generally exhibit increased circulatory lifetime in vivo compared to large particles. In one embodiment, the lipid particle has a diameter from about 15 to about 50 nm.

In embodiments, the lipid nanoparticles of the invention are substantially homogeneous in their size distribution. In certain embodiments, the lipid nanoparticles of the invention have a mean particle diameter standard deviation of from about 65 to about 25%. In one embodiment, the lipid nanoparticles of the invention have a mean particle diameter standard deviation of about 60, 50, 40, 35, or 30%. In some embodiments, the lipid nucleic acid particles of the invention have a PDI of about 0.01 to 0.3.

The lipid nanoparticles according to embodiments of the invention have nearly 100% of the nucleic acid used in the formation process is encapsulated in the nanoparticles. In one embodiment, the lipid nanoparticles have about 90 to about 95% of the nucleic acid used in the formation process encapsulated in the lipid nanoparticles (LNP).

In one aspect, the invention provides a method for making LNP containing a therapeutic agent.

A variety of manual methods have been developed to formulate LNP systems containing genetic drugs. These methods include mixing preformed LNP with nucleic acid therapeutic (NAT) in the presence of ethanol, or mixing lipid dissolved in ethanol with an aqueous media containing NAT, and result in LNP with NAT encapsulation efficiencies of 65-95%. The mixing can be done in bulk, or using pipette mixing, or in a "T Tube" with two streams of reagents meeting the middle and running down a pipe together. Both of these methods rely on the presence of cationic lipid to achieve encapsulation of NAT, and a stabilizing agent to inhibit aggregation and the formation of large structures. The properties of the LNP systems produced, including size and NAT encapsulation efficiency, are sensitive to a variety of formulation parameters such as ionic strength, lipid and ethanol concentration, pH, NAT concentration and mixing rates. In general, parameters such as the relative lipid and NAT concentrations at the time of mixing, as well as the mixing rates, are difficult to control using manual formulation procedures, resulting in variability in the characteristics of LNP produced, both within and between preparations.

Microfluidic mixing devices such as the NanoAssemblr™ series by Precision NanoSystems Inc. (Vancouver, Canada) enable controlled and rapid mixing of fluids on a nanoliter scale. Temperature, residence time, and solute concentration are controlled during the process of rapid microfluidic mixing applied in the synthesis of inorganic lipid particles, and can outperform manual systems in large scale production of nanoparticles.

Microfluidic two-phase droplet techniques have been applied to produce monodisperse polymeric microparticles for drug delivery or to produce large vesicles for the encapsulation of cells, proteins, or other biomolecules. The use of hydrodynamic flow focusing, a common microfluidic technique to provide rapid mixing of reagents, to create monodisperse liposomes of controlled size has been demonstrated. This technique has also proven useful in the production of polymeric nanoparticles where smaller, more monodisperse particles were obtained, with higher encapsulation of small molecules as compared to bulk production methods.

U.S. Application Pub. Nos. 20120276209 and 20140328759, by Cullis et al. describe methods of using small volume mixing technology and high quality LNP derived thereby. U.S. Application Pub. No. 20160022580 by Ramsay et al. describes more advanced methods of using small volume mixing technology and products to formulate different materials. U.S. Application Pub. No. 2016235688 by Walsh, et al. discloses microfluidic mixers with different paths and wells to elements to be mixed. PCT Publication WO2017117647 discloses microfluidic mixers with disposable sterile paths. PCT Publication No WO201711764 by Wild, Leaver and Taylor discloses bifurcating toroidal micromixing geometries and their application to micromixing. United States Design patents D771834, D771833 and D772427 by Wild and Weaver disclose cartridges for microfluidic mixers.

In embodiments of the invention, devices for biological microfluidic mixing are used to prepare the lipid nanoparticles and therapeutic formulations of the invention. Precision NanoSystems Inc., in Vancouver, Canada, manufactures and sells such devices. The devices include a first and second stream of reagents, which feed into the microfluidic mixer, and lipid nanoparticles are collected from the outlet, or in other embodiments, emerge into a sterile environment.

A suitable microfluidic mixing device includes one or more microchannels (i.e., a channel having its greatest dimension less than 1 millimeter). In one example, the microchannel has a diameter from about 20 to about 300 µm. In examples, at least one region of the microchannel has a principal flow direction and one or more surfaces having at least one groove or protrusion defined therein, the groove or protrusion having an orientation that forms an angle with the principal direction (e.g., a staggered herringbone mixer), as described in U.S. Application Pub. No. 2004/0262223. In examples, at least one region of the microchannel has bas-relief structures.

The lipid nanoparticles of the present invention may be used to deliver a therapeutic agent to a cell, in vitro or in vivo. In particular embodiments, the therapeutic agent is a nucleic acid, which is delivered to a cell using nucleic acid-lipid nanoparticles of the present invention. The methods and compositions may be readily adapted for the delivery of any suitable therapeutic agent for the treatment of any disease or disorder that would benefit from such treatment.

In certain embodiments, the present invention provides methods for introducing a nucleic acid into a cell. Preferred nucleic acids for introduction into cells are siRNA, mRNA, immune-stimulating oligonucleotides, plasmids, antisense and ribozymes. These methods may be carried out by contacting the particles or compositions of the present invention with the cells for a period of time sufficient for intracellular delivery to occur.

Typical applications include using well known procedures to provide intracellular delivery of siRNA to knock down or silence specific cellular targets. Alternatively applications include delivery of DNA or mRNA sequences that code for therapeutically useful polypeptides. In this manner, therapy is provided for genetic diseases by supplying deficient or absent gene products. Methods of the present invention may be practiced in vitro, ex vivo, or in vivo. For example, the compositions of the present invention can also be used for delivery of nucleic acids to cells in vivo, using methods which are known to those of skill in the art.

The delivery of siRNA, mRNA and plasmid nucleic acid therapeutics by a lipid particle of the invention is described below.

For in vivo administration, the pharmaceutical compositions are preferably administered parenterally (e.g., intraarticularly, intravenously, intraperitoneally, subcutaneously, intradermaly, intratrachealy, intraosseous or intramuscularly). In particular embodiments, the pharmaceutical compositions are administered intravenously or intraperitoneally by a bolus injection. Other routes of administration include topical (skin, eyes, mucus membranes), oral, pulmonary, intranasal, sublingual, rectal, and vaginal.

In one embodiment, the present invention provides a method of modulating the expression of a target polynucleotide or polypeptide. These methods generally comprise contacting a cell with a lipid particle of the present invention that is associated with a nucleic acid capable of modulating the expression of a target polynucleotide or polypeptide. As used herein, the term "modulating" refers to altering the expression of a target polynucleotide or polypeptide. Modulating can mean increasing or enhancing, or it can mean decreasing or reducing.

In related embodiments, the present invention provides a method of treating a disease or disorder characterized by overexpression of a polypeptide in a subject, comprising providing to the subject a pharmaceutical composition of the present invention, wherein the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof.

In related embodiments, the present invention provides a method of treating a disease or disorder characterized by underexpression of a polypeptide in a subject, comprising providing to the subject a pharmaceutical composition of the present invention, wherein the therapeutic agent is selected from an mRNA, a self-replicating DNA, or a plasmid, comprises a nucleic acid therapeutic that specifically encodes or expresses the under-expressed polypeptide, or a complement thereof.

Exemplary mRNA encodes the protein or enzyme selected from human growth hormone, erythropoietin, a 1-antitrypsin, acid alpha glucosidase, arylsulfatase A, carboxypeptidase N, a-galactosidase A, alpha-L-iduronidase, iduronate-2-sulfatase, iduronate sulfatase, N-acetylglucosamine-1-phosphate transferase, N-acetylglucosaminidase, alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, heparin-N-sulfatase, lysosomal acid lipase, hyaluronidase, galactocerebrosidase, ornithine transcarbamylase (OTC), carbamoyl-phosphate synthetase 1 (CPS 1), argininosuccinate synthetase (ASS 1), argininosuccinate lyase (ASL), arginase 1 (ARGI), cystic fibrosis transmembrane conductance regulator (CFTR), survival motor neuron (SMN), Factor VIII, Factor IX, meganucleases like TAL-ENS, Cas9 and self-replicating RNA's and low density lipoprotein receptors (LDLR).

In a further aspect, the invention provides a pharmaceutical composition comprising a lipid particle of the invention and a pharmaceutically acceptable carrier or diluent. Representative pharmaceutically acceptable carriers or diluents include solutions for intravenous injection (e.g., saline or dextrose). The composition can take the form of a cream, ointment, gel, suspension, or emulsion.

The following is a description of a representative lipid nucleic acid particle (LNP) system, device and method for making the LNP system, and method for using a LNP for delivering therapeutic agents.

Formulation of LNPs was performed by rapidly mixing a lipid-ethanol solution with an aqueous buffer inside a microfluidic mixer designed to induce chaotic advection and provide a controlled mixing environment at intermediate Reynolds number ($24 < Re < 1000$). The microfluidic channel has herringbone features or configured in a manner as shown in PCT Pub. No. WO/2017/117647 by Wild, Leaver and Taylor.

Particle sizes and "polydispersity index" (PDI) of the LNP were measured by dynamic light scattering (DLS). PDI indicates the width of the particle distribution. This is a parameter calculated from a cumulative analysis of the (DLS)-measured intensity autocorrelation function assuming a single particle size mode and a single exponential fit to the autocorrelation function. From a biophysical point of view, a PDI below 0.1 indicates that the sample is monodisperse (As a reference, PDI of the NIST standards are below 0.05).

The following embodiments are provided for the purpose of illustrating, not limiting, the claimed invention.

In certain embodiments, a stabilizing agent is present in the particle in an amount from about 0.1 to about 20 MOL %. In some embodiments, the stabilizing agent is a surfactant. In some embodiments, the stabilizing agent is a PEG Lipid.

In some embodiments, the stabilizing agent is present in the particle in an amount from about 0.5 to about 10 MOL %. In one embodiment, the stabilizing agent is present in the lipid nanoparticle at about 2.5 MOL %.

In a preferred embodiment, the stabilizing agent is polyoxyethylene (40) stearate. In another embodiment, the stabilizing agent is polyoxyethylene (20) oleyl ether. "Myrj52™" is a tradename for polyoxyethylene (40) stearate. It is sold by Sigma-Aldrich Canada Co.

In certain embodiments, the stabilizing agent is a polyethylene glycol-lipid. Suitable polyethylene glycol-lipids include PEG-modified phosphatidylethanolamine, PEG-modified phosphatidic acid, PEG-modified ceramides (e.g., PEG-CerC14 or PEG-CerC20), PEG-modified dialkylamines, PEG-modified diacylglycerols, PEG-modified dialkylglycerols. Representative polyethylene glycol-lipids include PEG-c-DOMG, PEG-c-DMA, and PEG-s-DMG. Many of these are for sale from NOF America Corporation, White Plains, N.Y. under brand names such as SUNBRIGHT® GM-020 (DMG-PEG) In some embodiments, stabilizing agent can be a non-ionic surfactant. In embodiments of the invention, the Stabilizing agent is a PEG-lipid is present at concentrations of 0 to 10 MOL %. In some embodiments, stabilizing agent can be vitamin E TPGS. In some embodiments the repeating PEG moiety has an average molecular weight of 1000-2000. In some embodiments molecular weight average of the PEG segment is 1700-2000 with n value (number of PEG repeating units) between 39-47.

In other preferred embodiments, the nucleic acid is a plasmid composed of double stranded deoxyribonucleic acid. A plasmid is a genetic structure that resides in a cell's cytoplasm (as opposed to the nucleic where the traditional cellular genetics reside) cell that can replicate independently of the chromosomes, typically a small circular DNA strand. This is not a normal mammalian genetic construct, but is used as a therapeutic option for replacing or restoring faulty genetic function in a cell. Plasmids can also be used to create novel cellular or animal models for medical research. An engineered plasmid will have, in addition to a replication origin (or not, depending on the intended use), restriction enzyme recognition sites, which allow breaking the circle to introduce new genetic material, and a selective marker such as an antibiotic resistance gene. A plasmid may be from 2,000 to about 1 million base pairs (bp). The larger the plasmid, the more susceptible it is to shearing forces, which increases the need for encapsulation.

As used herein, the term "about" is defined as meaning 10% plus or minus the recited number. It is used to signify that the desired target concentration might be, for example, 40 mol %, but that through mixing inconsistencies, the actual percentage might differ by +/−5 mol %.

As used herein, mole % or mol % relates to the number of atoms or molecules of each component, rather than just the mass. Specifically, 1 mole represents $6.022 \times 10^{23}$ atoms or molecules of substance. Moles are calculated by dividing the mass of the component by the component's atomic or molecular weight (which is determined by adding all of the atomic masses for the atoms in a chemical formula as found on the periodic table of the elements). The mole fraction is determined by dividing the moles of one component in a mixture by the total number of moles of all substances in the mixture. The mole fractions for all substances in a mixture will add up to 100 percent.

As used herein, the term "nucleic acid" is defined as a substance intended to have a direct effect in the diagnosis, cure, mitigation, treatment or prevention of disease, or to have direct effect in restoring, correcting or modifying physiological functions, or to act as a research reagent. In preferred embodiments, the nucleic acid is an oligonucleotide.

In preferred embodiments, the therapeutic agent is a nucleic acid therapeutic, such as an RNA polynucleotide. In preferred embodiments, the therapeutic agent is double stranded circular DNA (plasmid).

As used herein, the term "research reagent" is defined by the fact that it has a direct influence on the biological effect of cells, tissues or organs. Research reagents include but are not limited polynucleotides, proteins, peptides, polysaccharides, inorganic ions and radionuclides. Examples of nucleic acid research reagents include but are not limited to anti-sense oligonucleotides, ribozymes, microRNA, mRNA, ribozyme, tRNA, tracrRNA, sgRNA, snRNA, siRNA, shRNA, ncRNA, miRNA, mRNA, pre-condensed DNA, pDNA or an aptamer. Nucleic acid Research Reagents are used to silence genes (with for example siRNA), express genes (with for example mRNA), edit genomes (with for example CRISPR/Cas9).

In this disclosure, the word "comprising" is used in a non-limiting sense to mean that items following the word are included, but items not specifically mentioned are not excluded. It will be understood that in embodiments which comprise or may comprise a specified feature or variable or parameter, alternative embodiments may consist, or consist essentially of such features, or variables or parameters. A reference to an element by the indefinite article "a" does not exclude the possibility that more than one of the elements is present, unless the context clearly requires that there be one and only one of the elements.

In this disclosure, "transfecting reagent" means a composition that enhances the transfer of nucleic acid into cells. It typically includes a cationic lipid to associate with nucleic acid, and structural lipids. LIPOFECTIN™ and LIPOFECTAMINE™ are legacy transfecting reagents incorporating cationic lipids like DOTMA. MESSENGER MAX™ LIPOFECTAMINE™ is a contemporary transfecting reagent sold by ThermoFisher. Lipofectamine® Messenger-MAX™ reagent is designed to transfect a higher amount of mRNA into neurons and difficult-to-transfect primary cells.

In this disclosure the recitation of numerical ranges by endpoints includes all numbers subsumed within that range including all whole numbers, all integers and all fractional intermediates (e.g., 1 to 5 includes 1, 1.5, 2, 2.75, 3, 3.80, 4, and 5 etc.). In this disclosure the singular forms an "an", and "the" include plural referents unless the content clearly dictates otherwise. Thus, for example, reference to a composition containing "a compound" includes a mixture of two or more compounds.

In this disclosure term "or" is generally employed in its sense including "and/or" unless the content clearly dictates otherwise.

The following examples are provided for the purpose of illustrating, not limiting, the invention.

EXAMPLES

Materials and Methods

Ammonium acetate, sodium acetate and sodium chloride were obtained from Fisher Scientific (Fair Lawn, N.J.). Cholesterol, stabilizer lipid "Myrj52™" or PEG (40) stearate, and triolein were purchased from Sigma-Aldrich (Oakville, Ontario). DiD is a lipid label used for visualizing lipid components. It is $DilC^{18}(5)$ stain (1,1'-Dioctadecyl-3,3,3',3'-Tetramethylindodicarbocyanine Perchlorate and available from Invitrogen (ThermoFisher Scientific, www.thermofisher.com web orders, product D-307).

The mRNA used was Enhanced Green Fluorescent Protein messenger RNA (EGFP mRNA) (5-methylcytidine, pseudouridine, Length: 996 nucleotides (SEQ ID No. 1) (from Trilink Biotechnologies, San Diego, Calif.), at 1.0 mg/mL in 10 mM Tris-HCl, pH 7.5. The unknown bases in SEQ ID NO. 1 are a portion of alpha globin which is a vendor trade secret.

RNase A was obtained from Applied Biosystems/Ambion (Austin, Tex.).

The siRNA used was Hypoxanthine phosphoribosyltransferase 1 siRNA rGrCrCrArGrArCrUrUrUrGrUrUrGrGrArUrUrUrGrArArATT rArArUrUrUrCrArArArUrCrCrArArCrArArArGrUrCrUrGrG rCrUrU an off-the-shelf dicer-substrate siRNA (DsiRNA) HPRT (SEQ ID NO 2, sense, SEQ ID NO 3, antisense)) and control siRNA DSiNC-1, a nonsilencing, negative control DsiRNA that does not recognize any sequences in human, mouse, or rat transcriptomes (SEQ ID NO 4, sense, SEQ ID NO 5, antisense). Both DsiRNA and DsiNC1 were purchased from Integrated DNA Technologies, Inc., Coralville, Iowa).

Structural lipid DOPE, structural lipid DSPC, and ionisable lipid 1,17-bis(2-octylcyclopropyl)heptadecan-9-yl 4-(dimethylamino) butanoate were purchased from Avanti Polar Lipids (Alabaster, Ala., USA), Methods Oligonucleotide or polynucleotide (siRNA, mRNA or plasmid, hereinafter referred to as "nucleic acid") solution was prepared in 25 mM-100 mM acetate buffer at pH 4.0. Depending on the desired oligonucleotide-to-lipid ratio and formulation concentration, solutions were prepared at a target concentration of 2.3 mg/ml to 4 mg/ml total lipid. A lipid solution containing 1,17-bis(2-octylcyclopropyl)heptadecan-9-yl 4-(dimethylamino)butanoate hydrochloride, DOPE, Myrj52 at 2.5 MOL %, and triolein was present at 10, 17.4 or 20 MOL %. DiD label was prepared in ethanol and mixed with the oligonucleotide or polynucleotide to achieve an ethanol concentration of 25% (v/v).

LNP were prepared by standard NanoAssemblr™ Benchtop™ procedure. The first stream included a therapeutic agent in acetate buffer. The second stream included lipid particle-forming materials in a second solvent. Suitable second solvents include solvents in which the cationic lipids are soluble and that are miscible with the first solvent. Representative second solvents include aqueous ethanol 90%, or anhydrous ethanol. Alternate second solvents include 1,4-dioxane, tetrahydrofuran, acetone, acetonitrile, dimethyl sulfoxide, dimethylformamide, acids, and other alcohols.

Following mixing in the microfluidic device, the LNP mixture was diluted into RNAse free tubes containing three to forty volumes of stirred phosphate buffered saline (PBS) buffer, pH 7.4. Ethanol was removed through dialysis in PBS, pH 7, or using Amicon™ centrifugal filters (Millipore, USA) at 3000 RPM. Once the required concentration for testing was achieved, the particles were filter sterilized using 200 um filters in aseptic conditions. "Empty" LNPs were similarly produced, with the oligonucleotide absent from the first buffer solution.

Sizing

Particle size is an important characteristic of LNP, because size dictates biodistribution in vivo. Particle size was determined by dynamic light scattering using a Zeta-Sizer Nano ZS™ (Malvern Instruments, UK).

RNA concentration and Encapsulation Efficiency were measured by a modified RiboGreen assay (Quant-IT-Ribogreen® Assay kit, Invitrogen). The RiboGreen® dye is a fluorescent nucleic acid stain for quantitating intact RNA. RiboGreen assay provides RNA quantitation with minimal consumption of sample. Encapsulation efficiency is defined as the percentage of RNA protected within the LNP. Briefly, standards and samples were prepared in a 96 well plate with and without 1% Triton-X100, and incubated at 37° C. for 15 minutes to break open the RNA LNPs. On completion of incubation, Ribogreen® reagent was added to samples and standards, and fluorescence intensities of standards and samples with and without Triton-X100 were measured (Exc. 485 nm/Em 520 nm). Percent Encapsulation or Encapsulation Efficiency is defined by the following equation:

$$\text{Encapsulation Efficiency} = [(\text{Total RNA} - \text{Free RNA (un-encapsulated RNA)}) / \text{Total RNA}]\%$$

For the culture of neurons, microsurgically dissected Cortex tissue from E18 Sprague Dawley rat was purchased from BrainBits, LLC, Springfield, Ill. This tissue was processed and the neuronal cells plated using the neuronal plating protocol from StemCell Technologies, Vancouver, BC. In short, the E18 cortex tissues were removed from the shipping medium and digested for 20 minutes using 0.25% trypsin. Following this, the trypsin was inactivated using DMEM media containing 10% FBS. The tissue was then pelleted and the FBS containing media was replaced with fresh DMEM. Following this, the tissue was again pelleted and the pellet was triturated in Neuronal Culture Media supplemented with SM1 (StemCell Technologies). The cell suspension was then passed through a 401 µM cell strainer to form a single cell suspension. The concentration of the cell suspension was assessed using trypan blue and a hemocytometer. The cell suspension was seeded at a density of $4.8 \times 10^4$ cells/cm² on PDL coated plates, or at a density of $3.2 \times 10^4$ cells/cm² on PDL coated coverslips. The cells were incubated in a 37° C. incubator with 5% $CO_2$ and half of the media was changed with fresh media every 3-4 days. Confirmation of neuronal cell type was done using visual inspection of the culture by microscope, as well as positive MAP2 staining. (MAP2 is a marker of neuronal cells).

Cell Treatment

After 7 days in culture, neurons were treated with 2.51 g/mL of mRNA LNP and supplemented with 51 g/mL of ApoE (Peprotech Inc., USA). Best results were obtained when both mRNA and plasmid were added to human NPCs when they were seeded.

Thus when the cells were passaged, they were seeded in individual wells and then the APoE and LNP added immediately. Forty-eight hours after being seeded, the neurons were treated with 2.51 g/mL of mRNA LNP, and 24H after treatment, harvested for downstream assessment.

Immunocytochemistry

Cells were seeded at the appropriate density on PDL coated coverslips. After treatment and incubation, the cells were fixed by 4% paraformaldehyde, permeabilized using 0.1% Triton X-100 in PBS, and then blocked using 10% normal donkey serum. Following blocking, primary antibody was added—MAP2 (Invitrogen)—and incubated overnight at 4° C. The following day, primary antibody was removed and secondary antibody was added as well as DAPI to stain the nucleus. The coverslips were then mounted on glass slides using ProLong Diamond™ fixative, (ThermoScientific, Waltham, Mass.). Images were acquired using a confocal microscope.

Viability

Cells were seeded at the appropriate density in 96 well plates in a final media volume per well of 100 μl. Following treatment and incubation time, 10 μl of medium was removed and 10 μl of PrestoBlue® cell viability reagent (ThermoScientific), was added, and the plate was incubated for 30 minutes at 37° C. before being read using a plate reader (Synergy H1 plate reader (BioTek, Winooski, Vt.)) using the reader specifications in the PrestoBlue® cell viability reagent.

Flow Cytometry

Following treatment and treatment incubation of neurons, the media from each well was collected and the cells were harvested using 0.25% trypsin. The trypsin was inactivated using 3% FBS in PBS, and the cells were pelleted in their corresponding media. Following centrifugation the cells were washed once with PBS and again pelleted. The cells were then resuspended in BD Pharmingen™ Binding Buffer, BD Biosciences (San Jose, Calif.), and Propidium Iodine was added to stain for cells with completely ruptured membranes, i.e. dead cells. The cells were then assessed using a BD Biosciences Canto II flow cytometer.

ELISA

Following treatment and treatment incubation of neurons, the cells were harvested following the protocol provided with SimpleStep™ GFP ELISA, AbCam. In short, the cells were washed with PBS and then lysed using the provided lysis buffer. Following lysis and collection the lysate was incubated on ice and then centrifuged to remove any remaining undigested cell debris. Total protein concentration was assessed using the BCA Protein Quantification Kit (AbCam, Cambridge, UK). The total protein concentration for each sample was then normalized to 1 ng/μl for use in the SimpleStep™ GFP ELISA.

Example 1

LNP Physical Characterization

Particle size (hydrodynamic diameter of the particles) was determined by Dynamic Light Scattering (DLS) using a ZetaSizer Nano ZS™, Malvern Instruments, UK). He/Ne laser of 633 nm wavelength was used as the light source. Data were measured from the scattered intensity data conducted in backscattering detection mode (measurement angle 173°). Measurements were an average of 10 runs of two cycles each per sample. Z-Average size was reported as the LNP size, and is defined as the harmonic intensity averaged particle diameter. Nucleic acid encapsulation was measured using the Ribogreen® dye method. A standard curve was established using known concentrations of control RNA sample, then test solutions were run and their measurements translated using the standard curve. Results are shown in Table 1.

TABLE 1

Physico-chemical parameters of GFP mRNA LNP Particles

| Formulation ID | Encap. Efficiency (%) | Size (nm) | PDI |
| --- | --- | --- | --- |
| Lipid Mix A | 98 | 87 | 0.12 |
| Lipid Mix G | 94 | 117 | 0.14 |
| Lipid Mix H | 93 | 134 | 0.13 |

Formulations contained various ratios of the cationic lipid 1,17-bis(2-octylcyclopropyl)heptadecan-9-yl 4-(dimethylamino)butanoate hydrochloride, structural lipids selected from DSPC and DOPE, Myrj52 as a stabilizing agent, and 0.5 MOL % of DiD. In Lipid Mix A, Lipid Mix G and Lipid Mix H, cholesterol was present. In Lipid Mix J, it was not. In Lipid Mix G, Lipid Mix H, and Lipid Mix J, triglyceride was present. In Lipid Mix A and D, triolein was not present. All of the formulations shown in Table 2 formed LNP with good size and PDI characteristics.

TABLE 2

Lipid Component Ratios

| Lipid Mix | Ratios in Mol % |
| --- | --- |
| A | 50/10/37.5/0/2.5 cationic lipid/DSPC/Cholesterol/Triglyceride/Stabilizing agent |
| D | 40/40/17.5/0/2.5 cationic lipid/DOPE/Cholesterol/Triglyceride/Stabilizing agent |
| G | 40/30/17/10/2.5 cationic lipid/DOPE/Cholesterol/Triglyceride/Stabilizing agent |
| H | 40/20/17/20/2.5 cationic lipid/DOPE/Cholesterol/Triglyceride/Stabilizing agent |
| J | 40/40/0/17.4/2.5 cationic lipid/DOPE/Cholesterol/Triglyceride/Stabilizing agent |

Example 2

Viability of Neurons Under Different Conditions—PrestoBlue Assay

Lipid Mix G and Lipid mix D mRNA LNP with GFP were compared to industry standard Lipofectamine® MessengerMax™ transfection reagent under seven conditions at 48 h:

no treatment (control)

treatment with Lipid Mix G GFP mRNA LNP at 2.5 ug/mL LNP+5 ug/mL ApoE;

treatment with Lipid Mix G GFP mRNA LNP at 5 ug/mL of LNP+5 ug/mL ApoE;

treatment with Lipid Mix H GFP mRNA LNP at 2.5 ug/mL of LNP+5 ug/mL ApoE;

treatment with Lipid Mix H GFP mRNA LNP at 5 ug/mL of LNP+5 ug/mL ApoE;

treatment with commercial reagent MessengerMax™ Lipofectamine™ at 1 ug/mL of Messenger Max™+5 ug/mL ApoE LNP; and treatment with commercial reagent MessengerMax™ Lipofectamine™ at 2.5 ug/mL of Messenger Max™+5 ug/mL ApoE LNP.

Results are shown in FIG. 1 as a bar graph of in vitro neuron viability demonstrated by PrestoBlue assay. Viability of neurons was well maintained by the Lipid Mix G and H LNP.

Example 3 siRNA in Lipid Nanoparticles (LNP)

siRNA Encapsulation was accomplished as set out in Methods above.

TABLE 3

Physicochemical Characteristics Of Sirna Nanoparticles

| Sample | Encapsulation Efficiency | Size | PDI |
|---|---|---|---|
| Lipid Mix A HPRT siRNA | 96.7 | 57.8 | 0.06 |
| Lipid Mix G HPRT siRNA | 88.4 | 79.95 | 0.15 |
| Lipid Mix H HPPRT siRNA | 93.3 | 76.84 | 0.07 |
| Lipid Mix A NC-1 siRNA | 97.5 | 58.8 | 0.07 | siRNA Transfection: Enriched neurons were treated with Lipid Nanoparticles (LNP) containing HPRT siRNA or control DS NC-1 siRNA in Lipid Mix A, Lipid Mix G, and Lipid Mix H. The LNP were made using the NanoAssemblr™ Spark™ micromixer or NanoAssemblr™ Benchtop micromixer, depending on the volume.

Uptake of HPRT siRNA was measured of Day 0, Day 2, Day 14 and Day 28. Knockdown of HPRT by said siRNA was measured at the same timepoints. Cell viability as tested by PrestoBlue™ assay across LNP concentrations (0-5000 ng/ml) indicated no toxicity for any of the conditions. Stability data of siRNA LNP generated up to 28 days indicated that the siRNA LNP was stable and that there was no change in activity/potency over this period. SiRNA LNP (1000, 100 and 10 ng/ml) along with a non-coding control siRNA formulation was used as a control when collecting the gene knockdown data.

Figure 2:
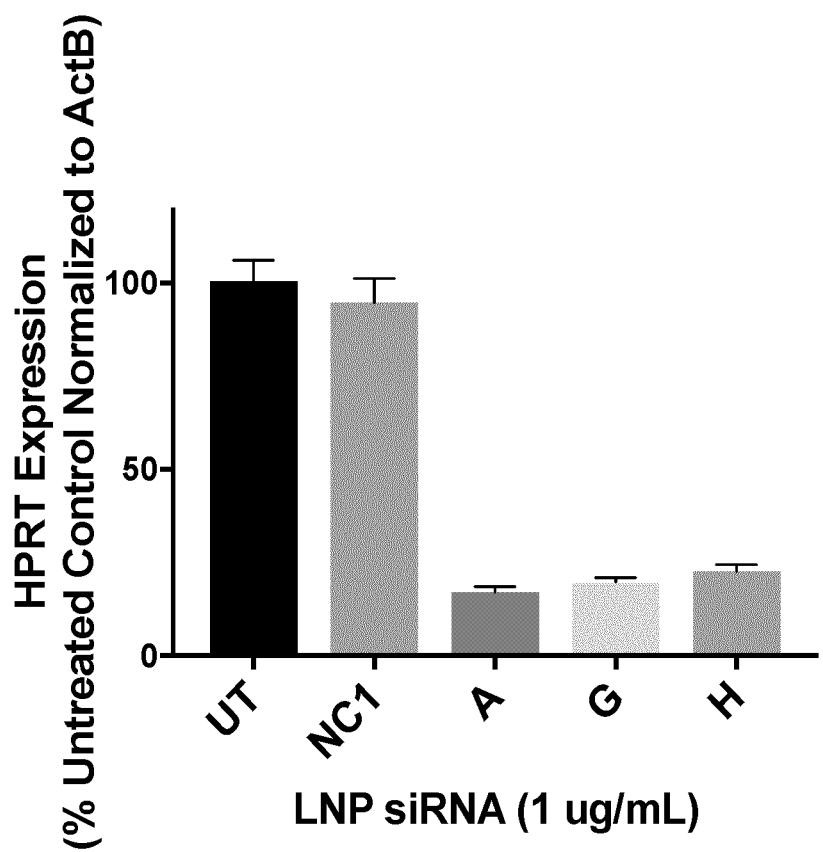
FIG. 2 is a graphical representation of percentage knock down of HPRT mediated by siRNA delivery to neurons using negative control siRNA (hereinafter "NC-1"), HPRT siRNA Lipid A LNP; HPRT siRNA Lipid Mix G LNP and HPRT siRNA Lipid Mix H LNP. HPRT expression is shown as a percent of untreated control (UT) and normalized to Beta actin (ActB)

Knockdown of HPRT as mediated by siRNA delivery to neurons using untreated (UT), negative control siRNA (DS NC-1) in Lipid Mix A, HPRT siRNA LNP incorporating Lipid Mix A; HPRT siRNA LNP incorporating Lipid Mix G, and HPRT siRNA LNP incorporating Lipid Mix H, with HPRT expression as a % of untreated control and normalized to ActB, is shown in FIG. 2. There is no substantial difference in the efficacy of delivery of siRNA among Lipid Mix A, Lipid Mix G, or Lipid Mix H nanoparticles.

Example 4 mRNA Transfection and Expression in Neurons—Confocal Microscopy

Messenger RNA and its post transfection activity was used to study the transfection ability of the nanoparticles. LNP Formulations Lipid Mix A, Lipid Mix G, and Lipid Mix H containing EGFP mRNA (GFP) were tested on enriched neurons, and GFP expression was assessed by confocal microscopy, flow cytometry, and ELISA. Encapsulation efficiency was established for LNP as set out in Table 1.

Figure 3:
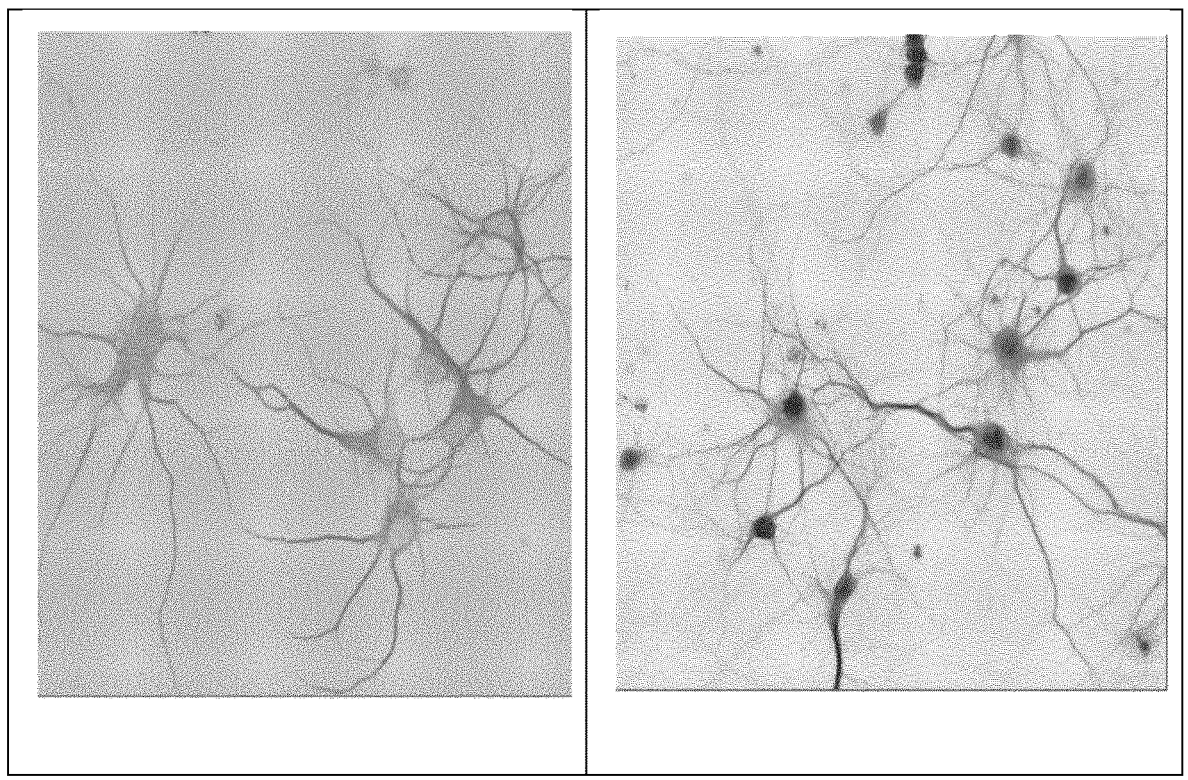
FIG. 3 is a black and white, image reversed photograph of neurons that have been exposed to Lipid Mix A LNP containing GFP mRNA (left panel), and Lipid Mix G formulated nanoparticles containing GFP mRNA (right panel). In both panels, MAP2 antibody staining (a neuronal marker) shows the outline of the neurons, DAPI stain shows the nuclei, and GFP expression in the neurons is shown as darkest staining. Merged images showing DAPI, MAP2, and GFP staining, establish GFP expression in the live neurons treated with Lipid Mix G LNP.

Fluorescence microscopy or confocal microscopy was used to identify GFP protein levels. FIG. 3 is a black and white, image reversed photograph of confocal microscopy of live neurons that have been treated with labeled Lipid Mix G LNP containing GFP. The reverse image showed the results better than the original colour photograph for black and white image. Both images include DAPI, a nuclear stain. The rightmost image shows MAP2 (a neuronal marker) antibody staining, and the leftmost image is a merge showing DiD, MAP2, and GFP in one image. In both panels, MAP2 antibody staining (a neuronal marker) shows the outline of the neurons. DAPI staining of the successfully delivered mRNA to the nuclei is dark in both the left and the right panel. GFP expression in the neurons is shown as even darker staining predominantly in the right panel. Not shown, no GFP expression was seen in neurons treated with Lipid Mix A mRNA LNP by the same confocal imaging process.

Lipid Mix G LNP was an effective mRNA delivery vehicle in live neurons.

Example 5

Flow Cytometry After Treatment with mRNA LNP

Figure 4:
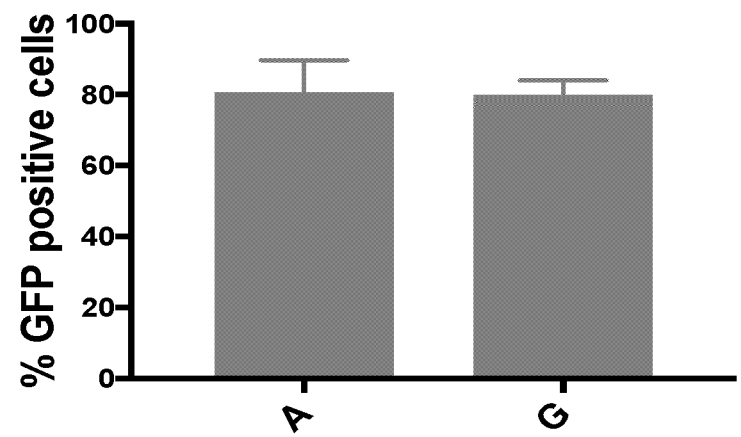
FIG. 4 is a graphical representation of the results obtained by flow cytometry analysis of neurons treated with Lipid Mix A and G encapsulating GFP mRNA. The first figure is a bar graph corresponding to the percentage of neurons positive for GFP, the second figure is a bar graph showing the mean fluorescent intensity of GFP expression in neurons treated with Lipid Mix A and Lipid Mix G nanoparticles (2.5 ug/mL of LNP+5 ug/mL ApoE)
Figure 4:
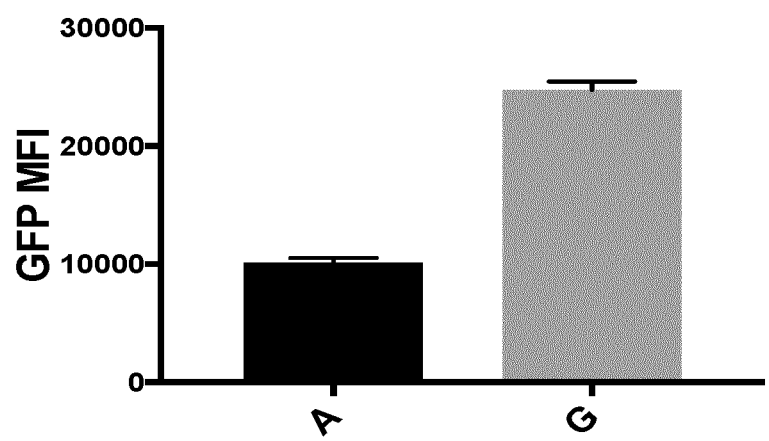

In FIG. 4, the upper bar graph shows the percentage of neurons positive for GFP expression obtained by flow cytometry analysis after treatment with Lipid Mix A and G GFP LNP respectively. The first bar graph in FIG. 4 corresponds to the percentage of neurons positive for GFP, while the lower bar graph shows the mean fluorescent intensity of GFP expression in neurons treated with Lipid Mix A and Lipid Mix G nanoparticles (2.5 ug/mL of LNP+5 ug/mL ApoE). Note how the expression of GFP is much greater for Lipid Mix G GFP LNP than Lipid Mix A GFP LNP. The MFI result is a better measure of degree of expression of the delivered mRNA, suggesting that Lipid Mix A is an inferior carrier when it comes to mRNA expression, despite working well for siRNA delivery.

Figure 5:
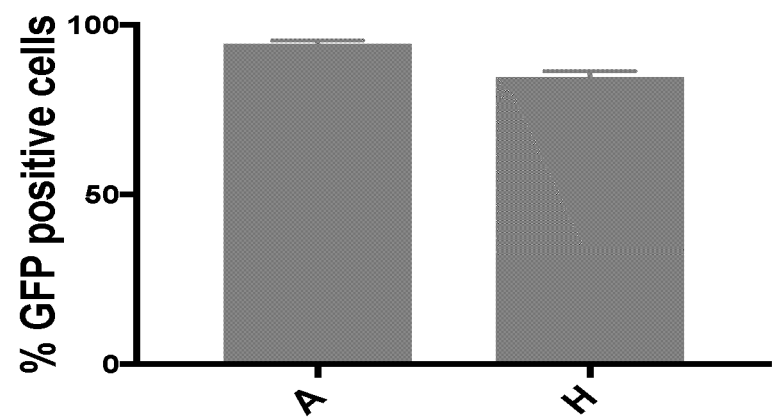
FIG. 5 is a graphical representation of the results obtained by flow cytometry analysis of neurons treated with Lipid Mix A and Lipid Mix H nanoparticles encapsulating GFP mRNA. The upper bar graph corresponds to the percentage of neurons that are positive for GFP, and the lower bar graph shows the mean fluorescent intensity of GFP expression in neurons treated with Lipid Mix A and Lipid Mix H nanoparticles (2.5 ug/mL of LNP+5 ug/mL ApoE)
Figure 5:
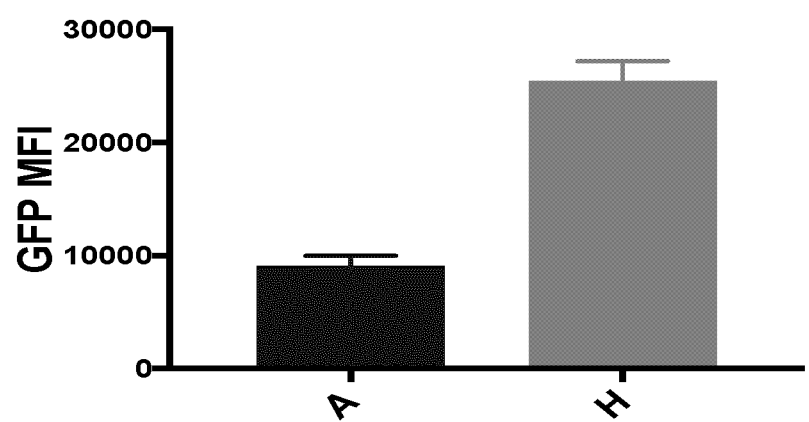

A similar comparison between Lipid Mix A GFP LNP and Lipid Mix H GFP LNP is shown in FIG. 5. The upper bar graph in FIG. 5 is the percentage of neurons with GFP present. Lipid Mix H gave better mRNA expression results, as shown in the lower MFI bar graph.

Example 6 mRNA Expression Established by ELISA

Figure 6:
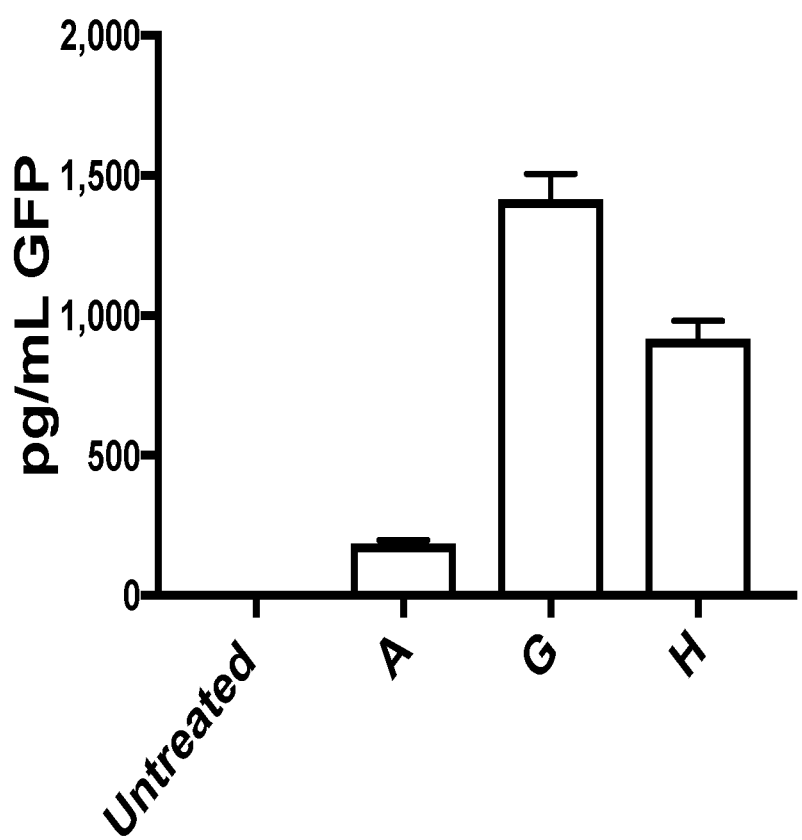
FIG. 6 is a graphical plot of GFP levels in pg/mL, measured by ELISA performed on DIV7 neurons 48 h post treatment with 2.5 ug/mL of LNP+5 ug/mL ApoE. The four bars represent the amount of GFP detected in untreated neurons, in neurons treated with Lipid Mix A, Lipid Mix G and Lipid Mix H mRNA LNP respectively from left to right.

The results of ELISA analysis of the levels of GFP expression levels (pg/mL) in DIV7 neurons transfected with 2.5 ug/mL of LNP+5 ug/mL ApoE are shown in FIG. 6. The four bars represent, respectively, the amount of GFP detected in a) untreated neurons, b) neurons treated with Lipid Mix A GFP LNP, c) neurons treated with Lipid Mix G GFP LNP, and d) neurons treated with Lipid Mix H GFP LNP. Lipid Mix A performs little better than no treatment, while Lipid Mix G and H produced excellent GFP expression results.

Example 7

Plasmid Encapsulated LNP Characteristics

Plasmid preparation pCMV-GFP (3487 bp, circular, double stranded DNA, SEQ ID. No. 6), Kanamycin resistant, was ordered from PlasmidFactory, Germany, and stored in water for injection. The plasmid included a GFP reporter gene which produces target protein only when the plasmid is successfully expressed within a cell. The physical characteristics of plasmid LNP using Lipid Mix A, G, H and J are shown in Table 4. The size and PDI of the manufactured LNPs with Lipid Mix A, G, H and J were very similar.

TABLE 4

Plasmid LNP Particles: Physico-chemical parameters

| Formulation ID | Encapsulation Efficiency (%) | Size | PDI |
|---|---|---|---|
| Lipid Mix A | 89.2 | 76.67 | 0.055 |
| Lipid Mix G | 97.5 | 96.7 | 0.132 |
| Lipid Mix H | 97.8 | 98.75 | 0.11 |
| Lipid Mix J | 98.1 | 99.59 | 0.14 |

Example 8

Plasmid Expression In Vitro

Figure 7:
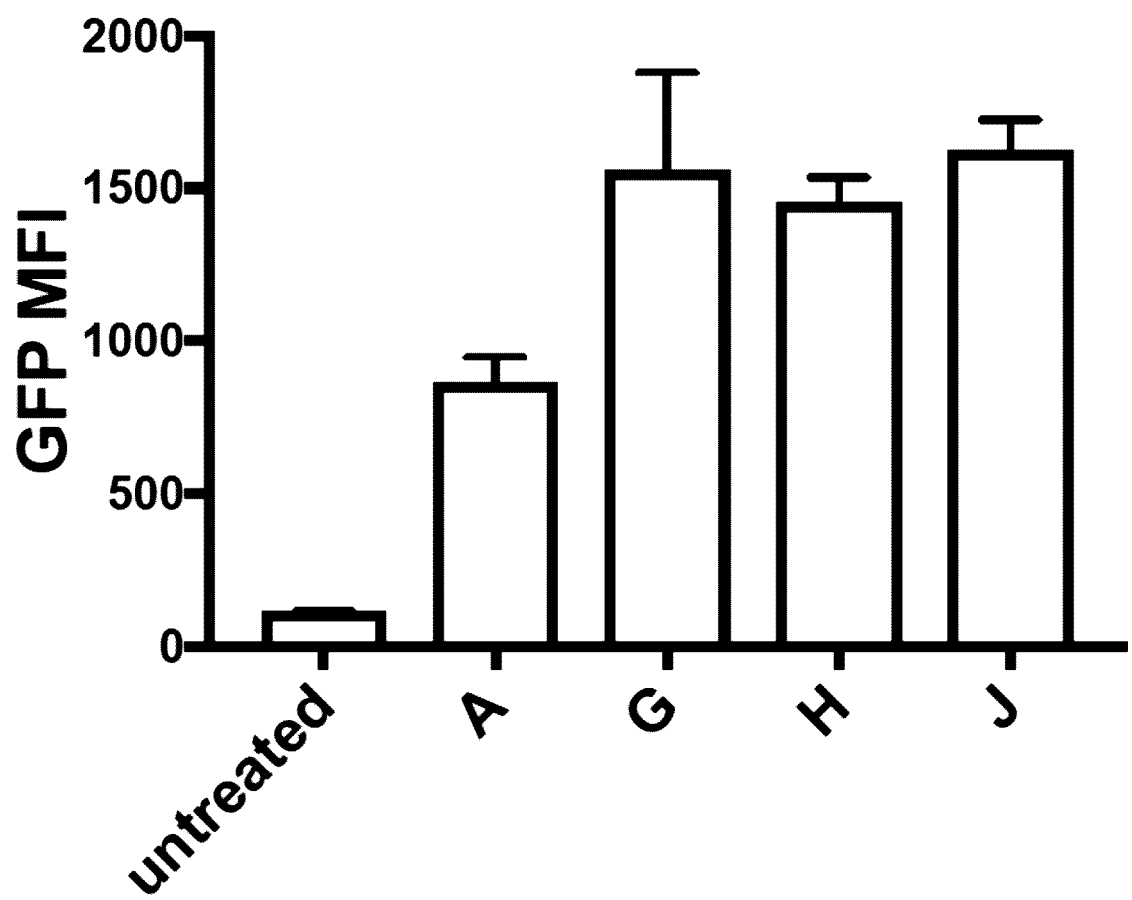
FIG. 7 is a graphical representation of flow cytometry of GFP-expressing plasmid DNA in transfection into neuron cells using the Lipid Mixes A, G, H and J. The mean fluorescent intensity of MFI indicates the amount of GFP expression mediated by different nanoparticle formulations. The concentrations of treatment nanoparticles was 1 ug/ml of LNP with 5 ug/ml ApoE.
Figure 8:
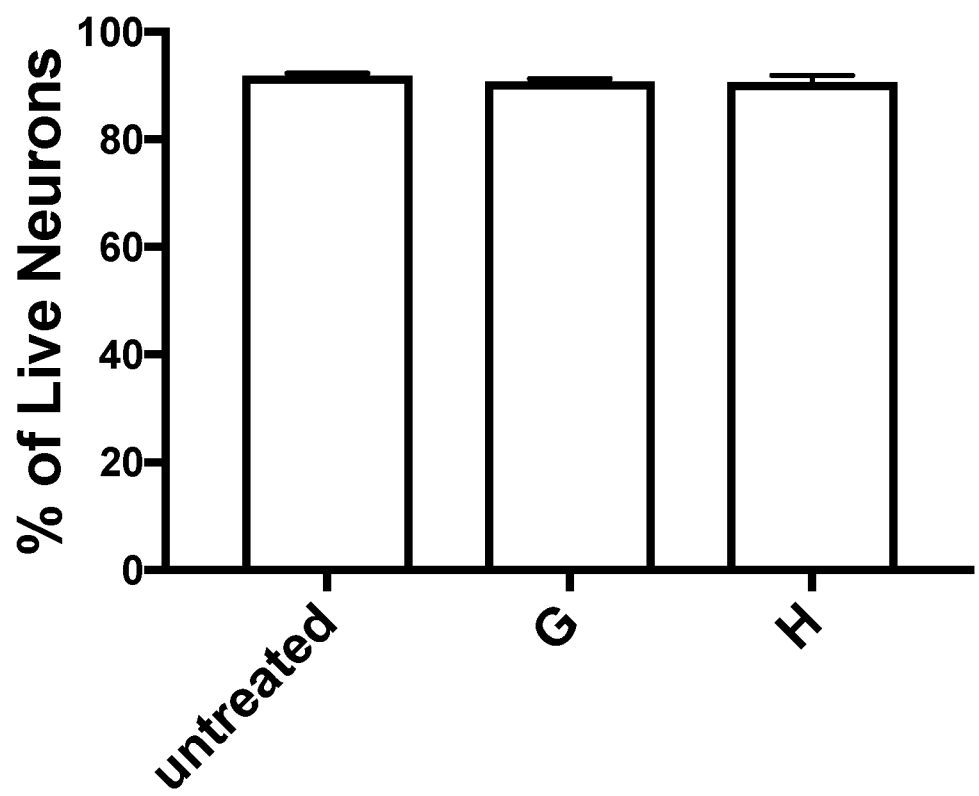
FIG. 8 is a graphical rendition of flow cytometry viability data of DIV7 neurons exposed to the various plasmid DNA nanoparticles, measured 48 h post exposure. Data is shown for plasmid containing lipid nanoparticles untreated control, Lipid Mix G, and Lipid Mix H at 1 ug/mL LNP and 5 ug/mL ApoE.

Lipid Mix A, Lipid Mix G, Lipid Mix H and Lipid Mix J LNP with pCMV-GFP plasmid encapsulated were added to cell cultures of neurons (DIV7) as described in Methods above, for 48 hours. Excellent expression was noted in the cell cultures treated with Lipid Mix G, Lipid Mix H and Lipid Mix J, as measured by mean fluorescence intensity (MFI) by flow cytometry. Results are shown in FIG. 7. Viability of the cells was not reduced by any of the formulations (as compared to untreated) for plasmid containing lipid nanoparticles comprised of Lipid Mix G, and Lipid Mix H at 1 ug/mL LNP and 5 ug/mL ApoE, as shown in FIG. 8.

Example 9

Cholesterol, Regardless of Source, had No Effect

Cholesterol had been understood to be a helpful additive in LNP formulations.

However, in our tests, it appears to be nonessential. Testing and validation of cholesterol and surfactant (namely Myrj52) showed a reduction in LNP size (~60 nm) and PDI (~0.08) with the addition of surfactant and cholesterol. LNP comprised of Lipid Mix J is a cholesterol-free triolein formulation capable of transfecting neurons with plasmid DNA as shown in FIG. 7.

Example 10

In Vivo Comparison of mRNA Expression

C57BL/6 mice were treated at a dose of 1 mg/kg (iv) of Lipid Mix D GFP LNP or Lipid Mix G GFP LNP; GFP expression was quantified using the GFP ELISA protocol in Methods above.

Figure 9:
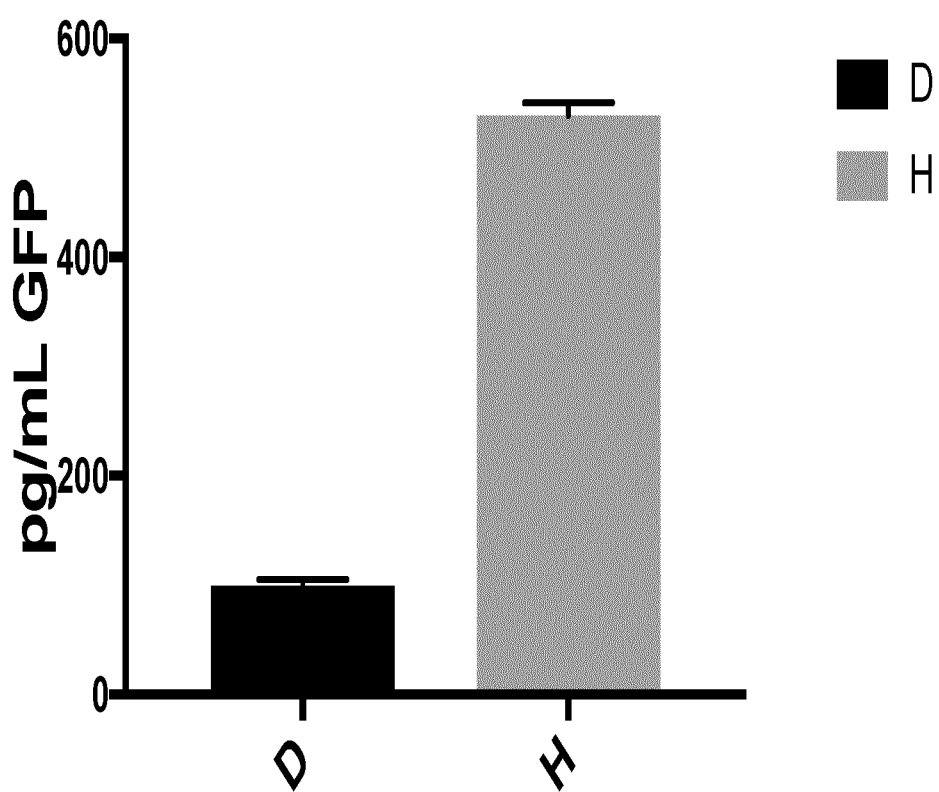
FIG. 9 is a graphical representation of GFP expression in vivo in pg/mL, in spleen from the mRNA treated C57BL/6 mice at a dose of 1 mg/kg (iv) using particles of Lipid Mix D and Lipid Mix H; GFP expression was quantified using GFP ELISA kit.

Mice were sacrificed and their spleens harvested. Spleen tissue tested for GFP levels. Results shown in pg/mL in FIG. 9. Results are shown for Lipid Mix D LNP and Lipid Mix H LNP. The triolein-containing LNP gives substantially better expression of the mRNA than Lipid Mix D LNP.

While specific embodiments of the invention have been described and illustrated, such embodiments should be considered illustrative of the invention only and not as limiting the invention as construed in accordance with the accompanying claims.

BIBLIOGRAPHY

Akhtar, S., E. Basu S Fau-Wickstrom, R. L. Wickstrom E Fau-Juliano and R. L. Juliano (1991). "Interactions of antisense DNA oligonucleotide analogs with phospholipid membranes (liposomes)." (0305-1048 (Print)).

Kauffman, K. J., M. J. Webber and D. G. Anderson (2015). "Materials for non-viral intracellular delivery of messenger RNA therapeutics." *J Control Release*.

Kaufmann k, Dorkin Robert J; Yang, Jung H; Heartlein, Michael W; De Rosa, Frank; Mir, Faryal F; Fenton, Owen S; Anderson, Daniel G (2015). "Optimization of Lipid Nanoparticle Formulations for mRNA Delivery in Vivo with Fractional Factorial and Definitive Screening Designs." *Nano Letters* 15: 7300-7306.

Lv, H., S. Zhang, B. Wang, S. Cui and J. Yan (2006). "Toxicity of cationic lipids and cationic polymers in gene delivery." *Journal of Controlled Release* 114(1): 100-109.

Mingozzi, F. and K. A. High (2013). "Immune responses to AAV vectors: overcoming barriers to successful gene therapy." *Blood* 122(1): 23-36.

O'Mahony, A. M., B. M. Godinho, J. F. Cryan and C. M. O'Driscoll (2013). "Non-viral nanosystems for gene and small interfering RNA delivery to the central nervous system: formulating the solution." *J Pharm Sci* 102(10): 3469-3484.

Tam, Y. Y., S. Chen and P. R. Cullis (2013). "Advances in Lipid Nanoparticles for siRNA Delivery." *Pharmaceutics* 5(3): 498-507.

What is claimed:

1. A composition for transfecting nucleic acid into live cells comprising:
   (a) 40 mol % of a cationic lipid comprising 1,17-bis(2-octylcyclopropyl)heptadecan-9-yl-4-(dimethylamino) butanoate or a pharmaceutically acceptable salt thereof;
   (b) 20-40 mol % of a structural lipid, wherein the structural lipid is DOPE;
   (c) 10-20 mol % of a triglyceride, wherein the triglyceride is triolein; and
   (d) about 2.5 mol % of a stabilizing agent, wherein the stabilizing agent is polyoxyethylene (40) stearate.

2. The composition of claim 1, further comprising a sterol.

3. The composition of claim 2 wherein the sterol is cholesterol.

4. The composition of claim 1, further comprising a nucleic acid.

5. The composition of claim 4, wherein the nucleic acid is DNA, RNA, a locked nucleic acid, a nucleic acid analog, or a plasmid.

6. The composition of claim 4 wherein the nucleic acid is single or double stranded.

7. The composition of claim 4, wherein the composition exists in the form of nanoparticles having a diameter of from about 15 nm to about 300 nm.

8. A method for introducing a nucleic acid into a cell, for modulating the expression of a target polynucleotide or polypeptide in said cell while maintaining activity of the nucleic acid and viability of the cell, comprising contacting the cell with the composition of claim 4.

9. The method of claim 8, wherein the cell is a neuron or an astrocyte.

10. The method of claim 8 wherein the cell is a mammalian cell.

11. The method of claim 8, wherein the contacting occurs in vitro.

12. The method of claim 8, wherein the contacting occurs in vivo.

* * * * *